US012121208B2

(12) United States Patent
Saiga

(10) Patent No.: US 12,121,208 B2
(45) Date of Patent: Oct. 22, 2024

(54) ENDOSCOPE CONDUIT SWITCHING DEVICE, ENDOSCOPE, AND METHOD OF MANUFACTURING ENDOSCOPE CONDUIT SWITCHING DEVICE

(71) Applicant: OLYMPUS CORPORATION, Tokyo (JP)

(72) Inventor: Kazuya Saiga, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 901 days.

(21) Appl. No.: 16/951,219

(22) Filed: Nov. 18, 2020

(65) Prior Publication Data

US 2021/0076910 A1 Mar. 18, 2021

Related U.S. Application Data

(63) Continuation of application No. PCT/JP2019/019983, filed on May 20, 2019.

(30) Foreign Application Priority Data

May 21, 2018 (JP) ................................ 2018-097276

(51) Int. Cl.
*A61B 1/00* (2006.01)
*A61B 1/015* (2006.01)
*A61B 8/12* (2006.01)

(52) U.S. Cl.
CPC ...... *A61B 1/00068* (2013.01); *A61B 1/00137* (2013.01); *A61B 1/015* (2013.01); *A61B 8/12* (2013.01)

(58) Field of Classification Search
CPC . A61B 1/00068; A61B 1/00137; A61B 1/015; A61B 8/12; A61B 8/4444
See application file for complete search history.

(56) References Cited

U.S. PATENT DOCUMENTS 5,027,791 A * 7/1991 Takahashi .............. A61B 1/126 600/158
5,299,561 A * 4/1994 Yoshimoto ......... A61B 1/00068 600/159

(Continued)

FOREIGN PATENT DOCUMENTS

JP 2007-111266 A 5/2007
JP 2012-071022 A 4/2012

(Continued)

OTHER PUBLICATIONS

International Search Report dated Jul. 16, 2109 received in PCT/JP2019/019983.

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

An endoscope conduit switching device includes: a cap that is made of resin, the cap including a pressing surface to be pressed by an operator and a shaft hole formed on a surface of the cap on a side opposite to the pressing surface; and a shaft having one end that is inserted into the shaft hole of the cap and as other end that is inserted into a conduit of the endoscope. The cap is joined to the shaft with a first joint portion and a second joint portion that are spaced apart from each other along a direction in which the shaft extends.

13 Claims, 19 Drawing Sheets

(56) References Cited

U.S. PATENT DOCUMENTS 5,301,656 A * 4/1994 Negoro ................ A61B 1/0052
600/149
5,840,015 A * 11/1998 Ogino ................ A61M 1/7413
600/156
5,871,441 A * 2/1999 Ishiguro ................ A61B 1/122
600/159
6,398,722 B1 * 6/2002 Mitsumori ............ A61B 1/121
600/133
7,484,709 B2 * 2/2009 Efinger .............. A61M 39/225
604/167.03
9,161,680 B2 * 10/2015 Bellofatto ............ A61B 1/0011
9,307,890 B2 * 4/2016 Ouchi ...................... A61B 1/05
9,398,842 B2 * 7/2016 Furuta .................... A61B 1/015
9,408,523 B2 * 8/2016 Grudo ................ A61B 1/00103
9,585,545 B2 * 3/2017 Anderson .............. A61B 1/015
10,674,898 B2 * 6/2020 Anderson .............. A61B 1/015
10,898,062 B2 * 1/2021 Wolfe ................ A61B 1/00068
11,241,142 B2 * 2/2022 Saiga ................. A61B 1/00119
11,311,181 B2 * 4/2022 Wolfe ................ A61B 1/00068
2004/0238014 A1 * 12/2004 Halstead .................. A61L 2/18
134/146
2011/0298169 A1 * 12/2011 Nguyen ................. A61B 1/125
269/86
2012/0088975 A1 * 4/2012 Morimoto .......... A61B 1/00068
600/159
2013/0303844 A1 * 11/2013 Grudo ................ A61B 1/00105
600/101
2015/0144215 A1 * 5/2015 Bellofatto ........... F16K 11/0712
137/625.69
2015/0216393 A1 * 8/2015 Toyoda .............. A61B 1/00068
600/159
2017/0143194 A1 * 5/2017 Wolfe ................ A61B 1/00103
2017/0360278 A1 * 12/2017 Suzuki ............... A61B 1/00068
2020/0016637 A1 * 1/2020 Still ........................ A61B 1/125
2020/0077873 A1 * 3/2020 Wolfe ................ A61B 1/00103
2021/0076910 A1 * 3/2021 Saiga ................. A61B 1/00137

FOREIGN PATENT DOCUMENTS

JP 2012-071023 A 4/2012
JP 2013-116144 A 6/2013

* cited by examiner

ENDOSCOPE CONDUIT SWITCHING DEVICE, ENDOSCOPE, AND METHOD OF MANUFACTURING ENDOSCOPE CONDUIT SWITCHING DEVICE

CROSS-REFERENCE TO RELATED APPLICATIONS

This application is a continuation of PCT international application Ser. No. PCT/JP2019/019983, filed on May 20, 2019 which designates the United States, incorporated herein by reference, and which claims the benefit of priority from Japanese Patent Applications No. 2018-097276, filed on May 21, 2018, incorporated herein by reference.

BACKGROUND

1. Technical Field

The present disclosure relates to an endoscope conduit switching device, an endoscope, and a method of manufacturing an endoscope conduit switching device.

2. Related Art

In the related art, there is an ultrasound endoscope in which a flexible and elongated insertion portion is inserted into a subject such as a person and ultrasound waves are transmitted and received by an ultrasound transducer provided on the distal end side of the insertion portion to observe the inside of the subject.

In some cases, the ultrasound endoscope suctions a substance such as a liquid, which is present inside the body of the subject, through a tapered surface provided at the distal end of the insertion portion via a channel suction conduit that communicates from an operating portion provided on the proximal end side of the insertion portion to the distal end of the insertion portion. Further, in some cases, the ultrasound endoscope suctions a liquid inside a balloon through a balloon water filling port provided on the distal end of the insertion portion via a balloon suction conduit that communicates from the operating portion to the distal end of the insertion portion. An endoscope conduit switching device provided in the operating portion switches between the suction conduits (see, for example, Japanese Patent Application Laid-open No. 2007-111266).

SUMMARY

In some embodiments, an endoscope conduit switching device includes: a cap that is made of resin, the cap including a pressing surface to be pressed by an operator and a shaft hole formed on a surface of the cap on a side opposite to the pressing surface; and a shaft having one end that is inserted into the shaft hole of the cap and an other end that is inserted into a conduit of the endoscope. The cap is joined to the shaft with a first joint portion and a second joint portion that are spaced apart from each other along a direction in which the shaft extends.

In some embodiments, an endoscope includes: an endoscope main body including: an insertion portion to be inserted into a subject; and an operating portion provided on a proximal end side of the insertion portion, and the endoscope conduit switching device provided in the operating portion of the endoscope main body.

In some embodiments, provided is a method of manufacturing an endoscope conduit switching device. The endoscope conduit switching device includes: a cap that is made of resin, the cap including a pressing surface to be pressed by an operator and a shaft hole formed on a surface of the cap on a side opposite to the pressing surface; and a shaft having one end that is inserted into the shaft hole of the cap and an other end that is inserted into a conduit of the endoscope, the cap being joined to the shaft with a first joint portion and a second joint portion that are spaced apart from each other along a direction in which the shaft extends. The method includes: inserting the shaft into the shaft hole of the cap; disposing first resin to be melted and second resin to be melted between the cap and the shaft at two points spaced apart from each other along a direction in which the shaft extends, respectively; melting the first resin; allowing the melted first resin to flow around an area where the first resin is disposed such that the melted first resin surrounds the area so as to form the first joint portion; melting the second resin; and allowing the melted second resin to flow around an area where the second resin is disposed such that the melted second resin surrounds the area so as to form the second joint portion.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
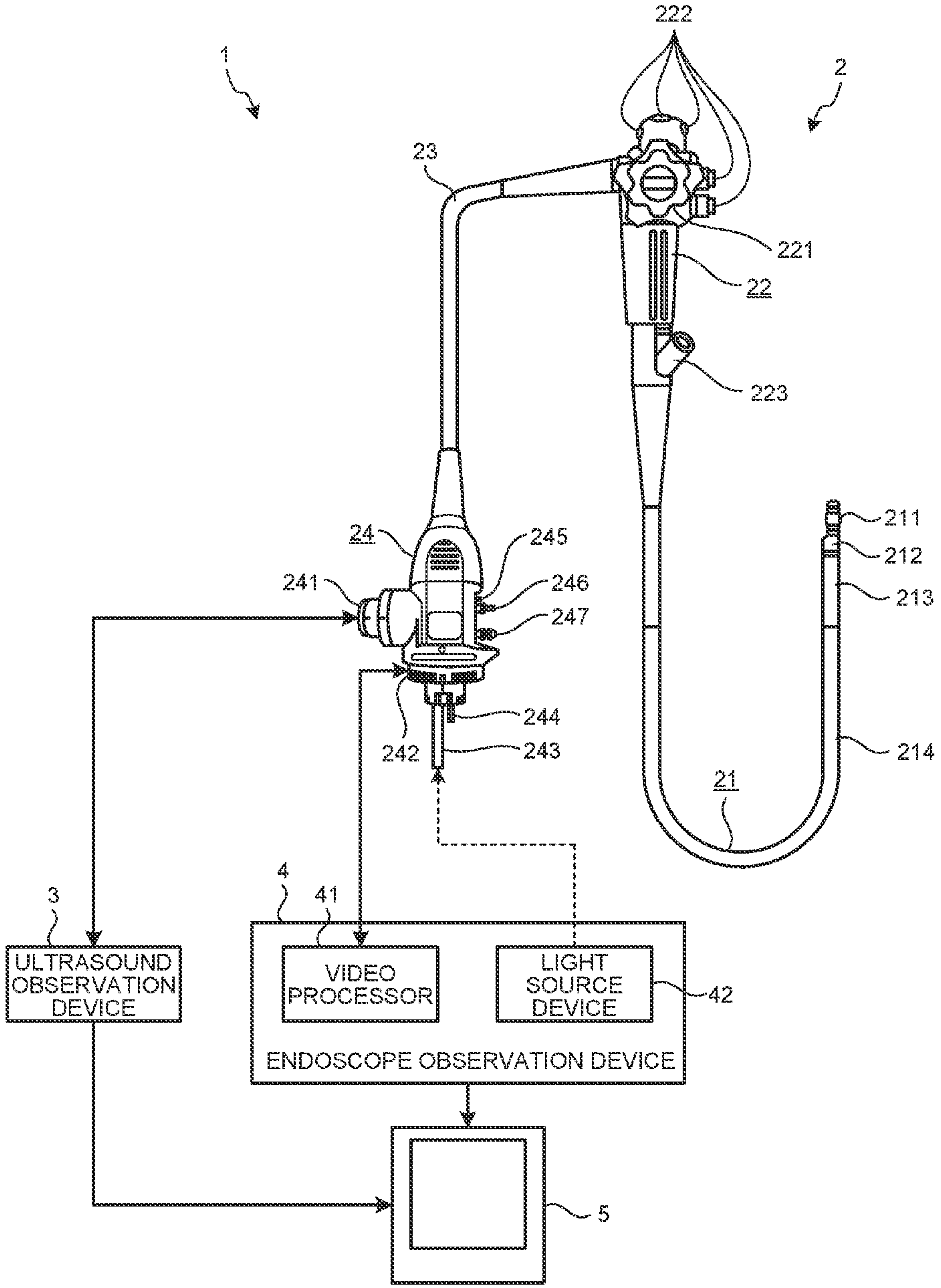
FIG. 1 is a diagram schematically illustrating an endoscope system according to an embodiment of the disclosure.

An embodiment of a disposable conduit switching device for an endoscope according to the disclosure is described below with reference to the drawings. It should be noted that the disclosure is not limited to the embodiment. In the description according to the embodiment below, a disposable conduit switching device for a medical endoscope is described as an example; however, the disclosure is applicable to typical disposable conduit switching devices for an endoscope including the ones for, for example, medical and industrial purposes.

In the description of the drawings, the identical or corresponding elements are denoted by the identical reference numeral as appropriate. It should be noted that the drawings are schematic and the dimensional relation between elements, the ratio of elements, and the like, are sometimes different from the reality in some cases. The drawings may include the parts that are different in the dimensional relation or the ratio.

EMBODIMENT

FIG. 1 is a diagram schematically illustrating an endoscope system 1 according to an embodiment of the disclosure. The endoscope system 1 illustrated in FIG. 1 is a system that executes ultrasound diagnosis on the inside of a subject, such as a person, by using an ultrasound endoscope. As illustrated in FIG. 1, the endoscope system 1 includes an ultrasound endoscope 2 (endoscope), an ultrasound observation device 3, an endoscope observation device 4, and a display device 5.

The ultrasound endoscope 2 functions as an endoscope according to the disclosure. The ultrasound endoscope 2 allows a part thereof to be inserted into the subject and has the function of transmitting an ultrasound pulse toward the body wall inside the subject, receiving an ultrasound echo reflected by the subject, and outputting an echo signal and the function of capturing the inside of the subject and outputting an image signal. The detailed configuration of the ultrasound endoscope 2 is described below.

The ultrasound observation device 3 is electrically connected to the ultrasound endoscope 2 via an ultrasound cable 31 to output a pulse signal to the ultrasound endoscope 2 via the ultrasound cable 31 and receive an echo signal from the ultrasound endoscope 2. The ultrasound observation device 3 executes predetermined processing on the echo signal to generate an ultrasound image.

The endoscope observation device 4 has an endoscope connector 24, described below, of the ultrasound endoscope 2 attachable to or detachable from the endoscope observation device 4. As illustrated in FIG. 1, the endoscope observation device 4 includes a video processor 41 and a light source device 42.

The video processor 41 receives an image signal from the ultrasound endoscope 2 via the endoscope connector 24. The video processor 41 executes predetermined processing on the image signal to generate an endoscope image.

The light source device 42 supplies, to the ultrasound endoscope 2, the illumination light for illuminating the inside of the subject through the endoscope connector 24.

The display device 5 is configured by using liquid crystal or organic electro luminescence (EL) to display an ultrasound image generated by the ultrasound observation device 3, an endoscopic image generated by the endoscope observation device 4, etc.

Next, a configuration of the ultrasound endoscope 2 is described with reference to FIGS. 1 to 5. As illustrated in FIG. 1, the ultrasound endoscope 2 includes an insertion portion 21, an operating portion 22, a universal cable 23, and the endoscope connector 24. The "distal end side" described below refers to the distal end side of the insertion portion 21 (the distal end side in the direction of insertion into the inside of the subject). The "proximal end side" described below refers to the side away from the distal end of the insertion portion 21.

The insertion portion 21 is a portion that is inserted into the subject. As illustrated in FIG. 1, the insertion portion 21 includes an ultrasound probe 211 provided on the distal end side, a rigid member 212 that is continuously connected to the proximal end side of the ultrasound probe 211, a bent portion 213 that is continuously connected to the proximal end side of the rigid member 212 and may be bent, and a flexible tube portion 214 that is flexible and is continuously connected to the proximal end side of the bent portion 213.

A light guide (not illustrated) for transmitting the illumination light supplied from the light source device 42 and signal cables (not illustrated) for transmitting the pulse signals, the echo signals, and the image signals described above extend inside the insertion portion 21, the operating portion 22, the universal cable 23, and the endoscope connector 24. The detailed configuration (the ultrasound probe 211 and the rigid member 212) on the distal end side of the insertion portion 21 is described below.

The operating portion 22 is a unit that is continuously connected to the proximal end side of the insertion portion 21 to receive various operations from a doctor, etc. As illustrated in FIG. 1, the operating portion 22 includes a bending knob 221 for bending the bent portion 213 and a plurality of operating members 222 for performing various operations.

Figure 3:
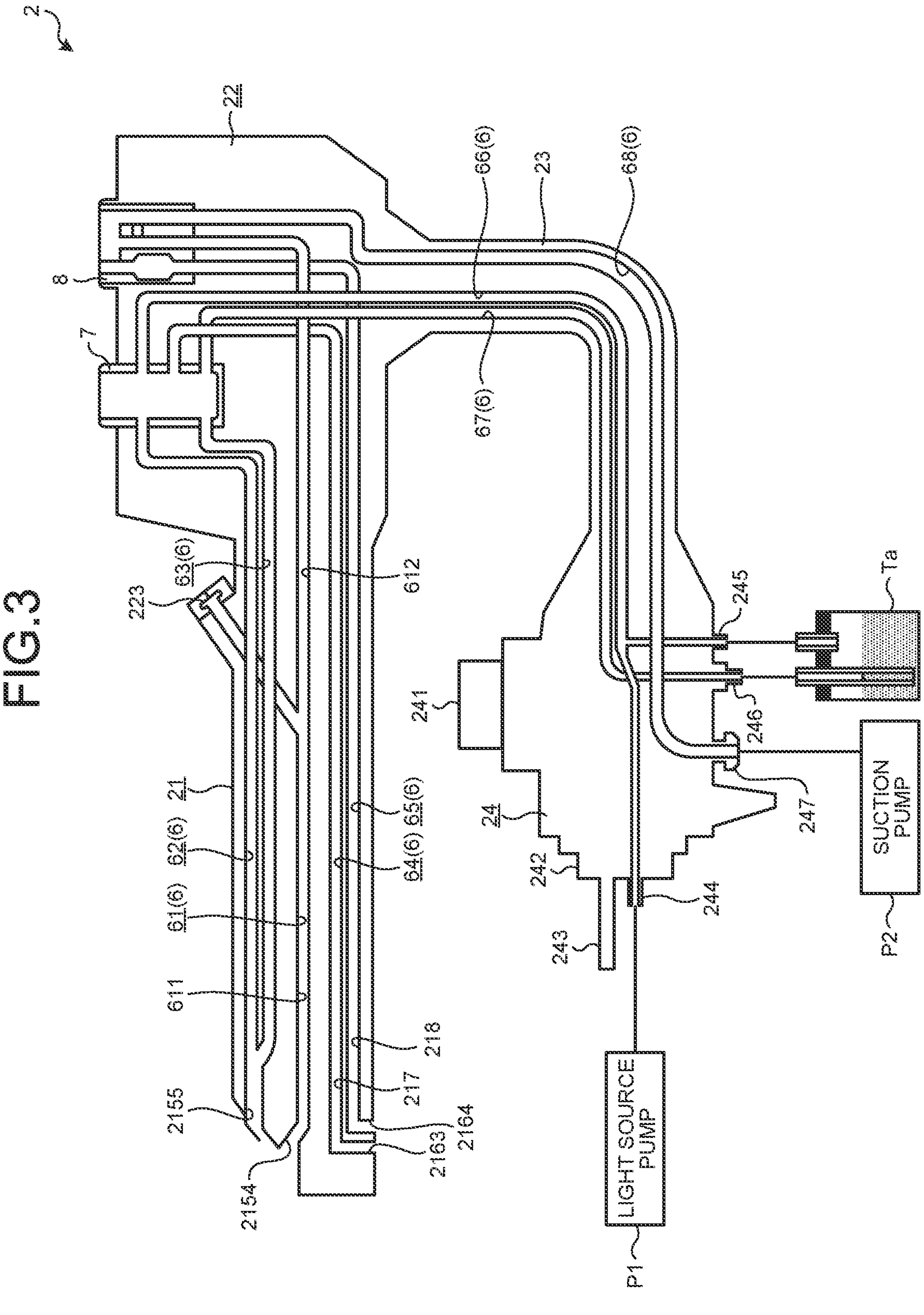
FIG. 3 is a diagram schematically illustrating a plurality of conduits provided in an ultrasound endoscope.

The insertion portion 21 and the operating portion 22 include distal-end side first to fifth conduits 61 to 65 (see FIG. 3). The operating portion 22 includes an air/water supply cylinder 7 and a suction cylinder 8 (see FIG. 6) that communicate with the distal-end side first to fifth conduits 61 to 65. The air/water supply cylinder 7 and the suction cylinder 8 include an air/water supply button 9 and a suction button 10 (see FIG. 8, etc.), respectively, which are disposable conduit switching devices for an endoscope that form a part of the operating members 222 and switch the connection state between the distal-end side first to fifth conduits 61 to 65 and proximal-end side first to third conduits 66 to 68 (see FIG. 3), described below, in accordance with an operation from a doctor, etc. The suction button 10 corresponds to a disposable conduit switching device for an endoscope according to the disclosure. The detailed configuration of a plurality of conduits 6 is described below. The connection states of the conduits 6 in accordance with an operation on the suction button 10 is described below. A known structure (see, for example, Japanese Laid-open Patent Publication No. 2007-111266) may be used as the structures of the air/water supply cylinder 7 and the air/water supply button 9. Therefore, the description of the detailed structures of the air/water supply cylinder 7 and the air/water supply button 9 is omitted from the description below, and the connection states of the conduits 6 in accordance with an operation on the air/water supply button 9 is described with reference to FIG. 10, and the like.

The universal cable 23 is a cable that extends from the operating portion 22 and is provided with the light guide (not illustrated) and the signal cables (not illustrated) described above.

The endoscope connector 24 is provided at an end of the universal cable 23. The endoscope connector 24 includes an ultrasound connector 241 that is connected to an ultrasound cable (not illustrated) and a plug portion 242 that is inserted into the endoscope observation device 4 and is coupled to the video processor 41 and the light source device 42.

The operating portion 22, the universal cable 23, and the endoscope connector 24 include the proximal-end side first to third conduits 66 to 68 (see FIG. 3) that communicate with the air/water supply cylinder 7 and the suction cylinder 8 included in the operating portion 22.

The plug portion 242 includes a plurality of electrical contacts (not illustrated), a light guide ferrule 243, and an air supply ferrule 244. The electrical contacts are portions that are electrically connected to the video processor 41 when the endoscope connector 24 is inserted into the endoscope observation device 4.

The light guide ferrule 243 is a portion that has the incident end side of the above-described light guide (not illustrated) inserted therethrough and that optically connects the light guide and the light source device 42 when the endoscope connector 24 is inserted into the endoscope observation device 4.

The air supply ferrule 244 is a portion that is coupled to a light source pump P1 (see FIG. 3) provided inside the light source device 42 when the endoscope connector 24 is inserted into the endoscope observation device 4.

The endoscope connector 24 further includes: a pressure ferrule 245 and a water supply ferrule 246 that are each coupled to an external water supply tank Ta (see FIG. 3); and a suction ferrule 247 that is coupled to an external suction pump P2 (see FIG. 3).

Figure 2:
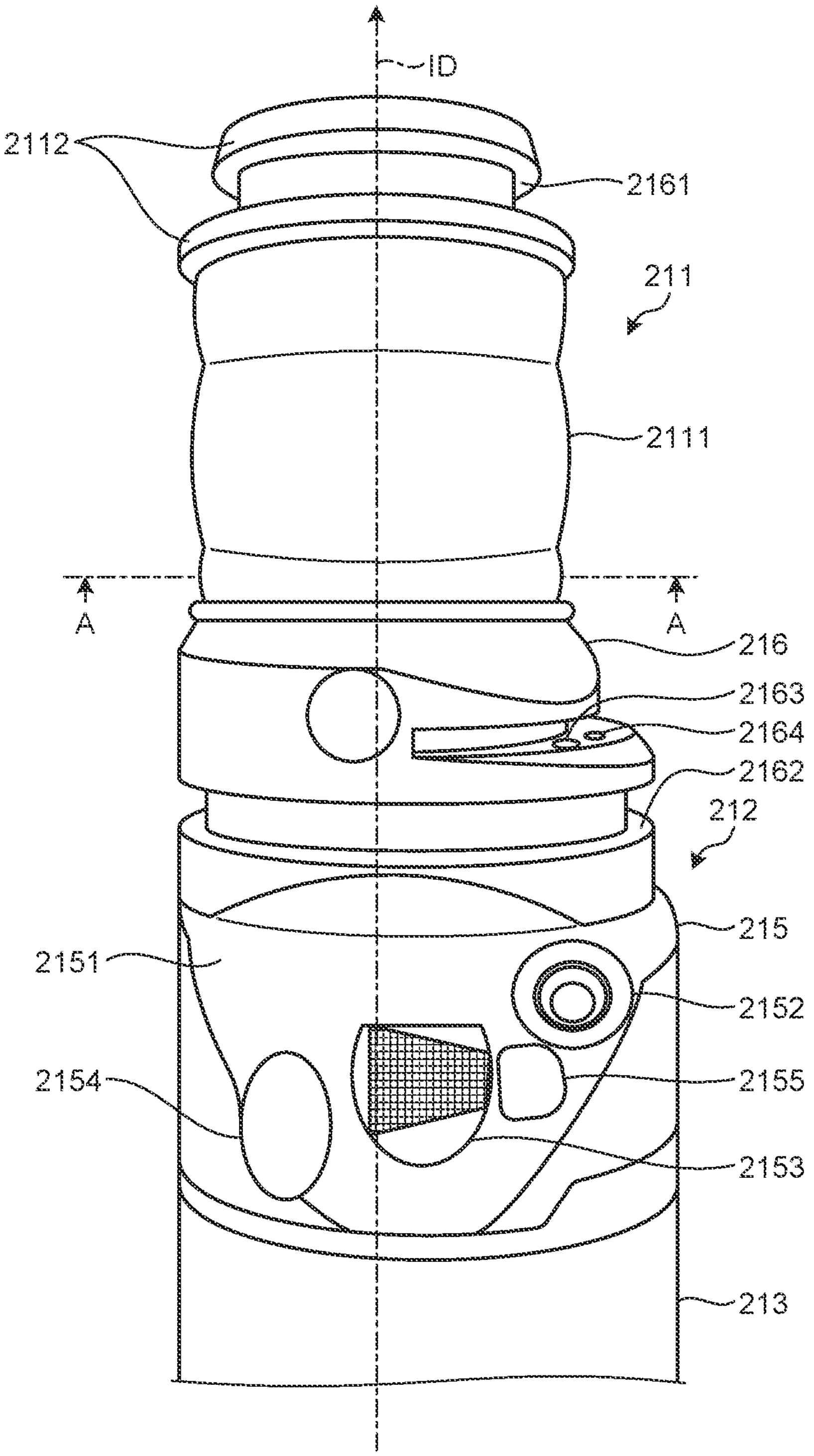
FIG. 2 is an enlarged view of a distal end side of an insertion portion.

FIG. 2 is an enlarged view of the distal end side of the insertion portion 21. The configurations of the ultrasound probe 211 and the rigid member 212 are sequentially described below with reference to FIG. 2.

The ultrasound probe 211 includes: a transducer unit 2111 having a plurality of ultrasound transducers regularly arranged; and a distal end portion 2112 that is made of a metal material or a resin material. The outer periphery of the distal end portion 2112 is provided with a balloon attachment groove 2161 for attaching a balloon (not illustrated) that may swell and shrink and has the inside thereof filled with water.

Figure 4:
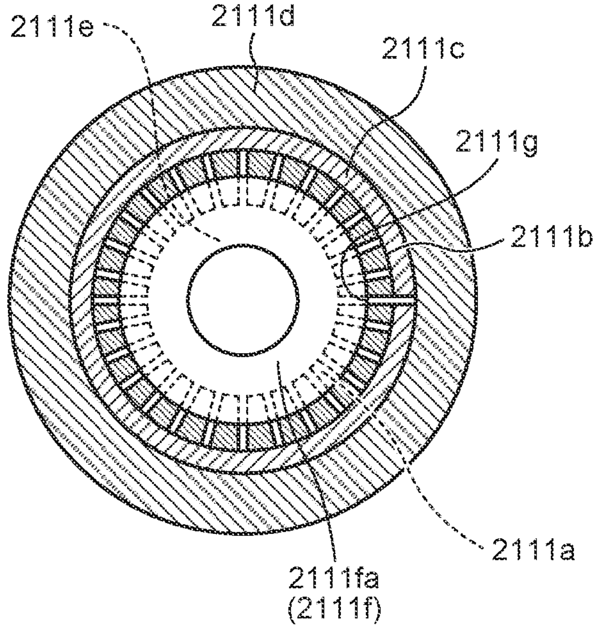
FIG. 4 is a diagram illustrating a configuration of an ultrasound probe according to the embodiment of the disclosure.
Figure 5:
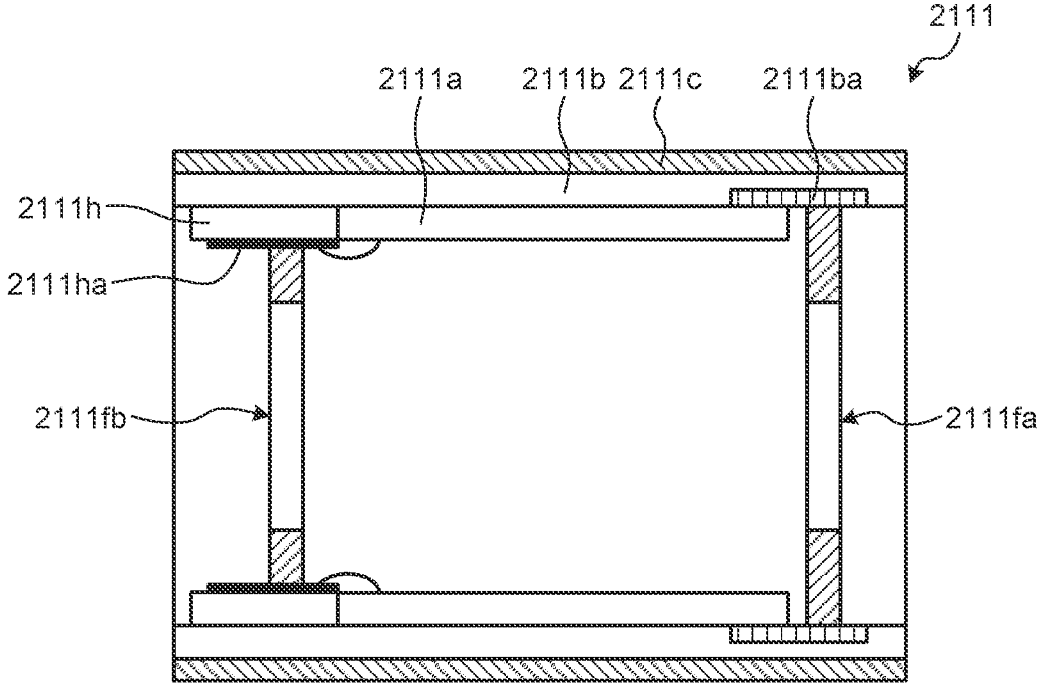
FIG. 5 is a diagram illustrating a configuration of the ultrasound probe according to the embodiment of the disclosure.

FIGS. 4 and 5 are diagrams illustrating the configuration of the ultrasound probe 211 according to the embodiment of the disclosure. FIG. 4 is a cross-sectional view corresponding to the line A-A of FIG. 2. FIG. 5 is a cross-sectional view of the transducer unit 2111 along the longitudinal direction of the insertion portion 21. As illustrated in FIGS. 4 and 5, the ultrasound probe 211 includes: a plurality of piezoelectric elements 2111*a* having the shape like a rectangular column, aligned in the longitudinal direction, and arranged in the circumferential direction; a plurality of first acoustic matching layers 2111*b* each provided on the inner peripheral surface side of the piezoelectric element 2111*a;* a second acoustic matching layer 2111*c* having substantially a tubular shape and provided on the side (outer surface side) of the first acoustic matching layer 2111*b* opposite to the side in contact with the piezoelectric element 2111*a;* an acoustic lens 2111*d* provided on the side of the second acoustic matching layer 2111*c* opposite to the side in contact with the first acoustic matching layer 2111*b;* a backing material 2111*e* provided on the side of the piezoelectric element 2111*a* opposite to the side in contact with the first acoustic matching layer 2111*b;* a structural member 2111*f* having the shape like a hollow circular disk and provided to maintain the shape of the ultrasound probe 211; a joint portion 2111*g* that joins the first acoustic matching layer 2111*b* and the second acoustic matching layer 2111*c;* and a substrate 2111*h* (see FIG. 5) electrically connected to the piezoelectric elements 2111*a.* According to the present embodiment, the first acoustic matching layer 2111*b* is provided for each of the piezoelectric elements 2111*a,* and the second acoustic matching layer 2111*c* and the acoustic lens 2111*d* collectively cover the piezoelectric elements 2111*a* and the first acoustic matching layer 2111*b.* According to the present embodiment, the configuration is such that the inside of the piezoelectric elements 2111*a* is filled with the backing material 2111*e.* The ultrasound probe 211 may use the single piezoelectric element 2111*a* or the multiple piezoelectric elements 2111*a* as a unit of output.

The ultrasound probe 211 is manufactured as follows: the sheet-like second acoustic matching layer 2111*c* having the piezoelectric elements 2111*a* and the first acoustic matching layers 2111*b* arranged thereon is rolled such that the piezoelectric elements 2111*a* are located on the inner circumference side so that the second acoustic matching layer 2111*c* is deformed into a tubular shape, the structural member 2111*f* is disposed, an adhesive is applied to the gap formed at two ends of each of the first acoustic matching layer 2111*b* and the second acoustic matching layer 2111*c* with respect to the arrangement direction of the piezoelectric elements 2111*a* so that the first acoustic matching layer 2111*b* and the second acoustic matching layer 2111*c* are bonded to each other, the grooves formed in the piezoelectric elements 2111*a* and the first acoustic matching layers 2111*b* are filled with an adhesive (not illustrated), and then the inside of the piezoelectric elements 2111*a* is filled with the backing material 2111*e.*

The piezoelectric element 2111*a* converts an electrical pulse signal into an ultrasound pulse (acoustic pulse) to emit the ultrasound pulse to the subject and also converts an ultrasound echo reflected by the subject into an electrical echo signal represented using a voltage change to output the electrical echo signal. The piezoelectric element 2111*a* is formed by using a PZT ceramic material, a PMN-PT single crystal, a PMN-PZT single crystal, a PZN-PT single crystal, a PIN-PZN-PT single crystal, or a relaxor-based material. The PMN-PT single crystal is the abbreviation for the solid solution of lead magnesium niobate and lead titanate. The PMN-PZT single crystal is the abbreviation for the solid solution of lead magnesium niobate and lead zirconate titanate. The PZN-PT single crystal is the abbreviation for the solid solution of lead zinc niobate and lead titanate. The PIN-PZN-PT single crystal is the abbreviation for the solid solution of lead indium niobate, lead zinc niobate, and lead titanate. The relaxor-based material is the generic term for a three-component piezoelectric material obtained by adding lead-based complex perovskite, which is a relaxer material, to lead zirconate titanate (PZT) for the purpose of increasing a piezoelectric constant and a dielectric constant. The lead-based complex perovskite is represented as $Pb(B1,B2)O_3$, in which B1 is any one of magnesium, zinc, indium, and scandium, and B2 is any one of niobium, tantalum, and tungsten. These materials have excellent piezoelectric effects. For this reason, it is possible to reduce the value of electrical impedance even with a reduction in size, and it is preferable in terms of impedance matching with a film electrode provided in the piezoelectric element 2111*a*.

The first acoustic matching layer 2111*b* and the second acoustic matching layer 2111*c* match the acoustic impedance between the piezoelectric elements 2111*a* and the observation target in order to efficiently transmit the sound (ultrasound wave) between the piezoelectric elements 2111*a* and the observation target. The first acoustic matching layer 2111*b* and the second acoustic matching layer 2111*c* are made of different materials. In the description according to the present embodiment, it is assumed that the two acoustic matching layers (the first acoustic matching layer 2111*b* and the second acoustic matching layer 2111*c*) are included; however, there may be the single acoustic matching layer or three or more acoustic matching layers depending on the characteristics of the piezoelectric elements 2111*a* and the observation target.

More specifically, the second acoustic matching layer 2111*c* is made of epoxy resin blended with a silicone filler. The acoustic impedance may be adjusted by changing the blending ratio of silicone. The higher the ratio of silicone is, the smaller the acoustic impedance is. The ratio of silicone is, for example, 1% to 50%, and it is preferable to appropriately adjust the ratio depending on the characteristics of the ultrasound probe 211 and the characteristics of the epoxy resin.

The grooves formed in the piezoelectric elements 2111*a* and the first acoustic matching layers 2111*b* are filled with an adhesive (not illustrated). The adhesive is epoxy resin having a mixture of first particles having a particle diameter in the order of microns and second particles having a particle diameter in the order of nanometer. The first particles are, for example, silica. The second particles are, for example, alumina. The adhesive has a mixture of the first particles and the second particles by a percentage such as 1% to 50% such that the percentage of the first particles is higher than that of the second particles. The ultrasound probe 211 is reinforced due to the blending of the first particles, and the viscosity of the adhesive is adjusted due to the blending of the second particles so that the adhesive is prevented from adhering to an unnecessary area during manufacturing.

The acoustic lens 2111*d* is formed by using silicone, polymethylpentene, epoxy resin, polyetherimide, and the like, with one surface thereof formed to be convex or concave so as to have the function of narrowing ultrasound waves, output the ultrasound waves passed through the acoustic matching layer to the outside, or receive an ultrasound echo from the outside. The acoustic lens 2111*d* may be optionally provided, and the configuration may be such that the acoustic lens 2111*d* is not provided.

The backing material 2111*e* attenuates unnecessary ultrasound vibrations caused due to the operation of the piezoelectric elements 2111*a*. The backing material 2111*e* is formed by using a material having a high attenuation rate, e.g., epoxy resin in which a filler, such as alumina or zirconia, is dispersed, or a rubber in which the above-described filler is dispersed.

The structural member 2111*f* is shaped like a hollow circular disk having the outer diameter corresponding to the diameter of the circle formed by the first acoustic matching layers 2111*b*. Specifically, as illustrated in FIG. 5, the structural member 2111*f* includes: a first structural member 2111*fa* provided on one end side in the direction (longitudinal direction) perpendicular to the plane formed in the circumferential direction of the second acoustic matching layer 2111*c;* and a second structural member 2111*fb* provided on the other end side in the longitudinal direction of the second acoustic matching layer 2111*c*. The first structural member 2111*fa* is shaped like a hollow circular disk having the outer diameter corresponding to the diameter of the circle formed by the first acoustic matching layers 2111*b,* and one surface thereof is covered with a conductive material such as copper foil. The second structural member 2111*fb* is shaped like a hollow circular disk having the outer diameter corresponding to the diameter of the circle formed by the inner peripheral surfaces of the substrates 2111*h*.

The joint portion 2111*g* is a joint portion for joining after deforming the sheet-like second acoustic matching layer 2111*c* having the piezoelectric elements 2111*a* and the first acoustic matching layers 2111*b* arranged thereon into a tubular shape along the arrangement direction of the piezoelectric elements 2111*a*. The joint portion 2111*g* is made of the same material as that of the second acoustic matching layer 2111*c*. As a result, it is possible to reduce the effect of the joint portion 2111*g* on signals transmitted and received by the ultrasound probe 211.

The substrate 2111*h* is electrically connected to the piezoelectric element 2111*a* with an electrode 2111*ha* interposed therebetween. The substrate 2111*h* is secured to the electrode 2111*ha* with an adhesive (not illustrated). The adhesive is made of the same material as the adhesive filled in the grooves formed in the piezoelectric elements 2111*a* and the first acoustic matching layers 2111*b*. As a result, it is possible to reduce the effect of the joint portion 2111*g* on signals transmitted and received by the ultrasound probe 211.

The ultrasound probe 211 having the above-described configuration irradiates the observation target with ultrasound waves via the first acoustic matching layers 2111*b,* the second acoustic matching layer 2111*c,* and the acoustic lens 2111*d* when the piezoelectric elements 2111*a* vibrate due to an input pulse signal. On the side of the piezoelectric elements 2111*a* opposite to the side where the first acoustic matching layers 2111*b,* the second acoustic matching layer 2111*c,* and the acoustic lens 2111*d* are provided, the backing material 2111*e* attenuate the vibrations of the piezoelectric elements 2111*a* so that the vibration transmission of the piezoelectric elements 2111*a* is prevented. The ultrasound waves reflected from the observation target are transmitted to the piezoelectric elements 2111*a* via the first acoustic matching layers 2111*b*, the second acoustic matching layer 2111*c,* and the acoustic lens 2111*d.* The piezoelectric elements 2111*a* vibrate due to the transmitted ultrasound wave, and the piezoelectric elements 2111*a* convert the vibration into an electric echo signal and outputs the echo signal to the ultrasound observation device 3 via a wire (not illustrated).

The rigid member 212 is a rigid member made of a metallic material or resin material. The rigid member 212 includes a large-diameter portion 215 and a small-diameter portion 216.

The large-diameter portion 215 is a portion to which the bent portion 213 is coupled and has substantially a cylindrical shape extending in an insertion direction ID of the insertion portion 21. The upper side of the large-diameter portion 215 is provided with a tapered surface 2151 that gradually reduces the diameter of the large-diameter portion 215 toward the front end side. As illustrated in FIG. 2, the large-diameter portion 215 is provided with an illumination hole 2152, an imaging hole 2153, an instrument channel 2154, and an air/water supply hole 2155 each penetrating from the proximal end of the large-diameter portion 215 to the tapered surface 2151.

The emission end side of the above-described light guide (not illustrated) is inserted into the illumination hole 2152. The illumination light supplied from the light source device 42 is emitted to the inside of the subject via the illumination hole 2152.

An objective optical system (not illustrated) that condenses the light (object image) emitted from the light source device 42 and reflected by the inside of the subject and an image sensor (not illustrated) that captures the object image condensed by the objective optical system are disposed inside the imaging hole 2153. The image signal captured by the image sensor is transmitted to the endoscope observation device 4 (the video processor 41) via the above-described signal cable (not illustrated).

The instrument channel 2154 forms part of the distal-end side first conduit 61.

The air/water supply hole 2155 forms part of the distal-end side second conduit 62 and the distal-end side third conduit 63.

The small-diameter portion 216 has substantially a cylindrical shape (substantially a cylindrical shape having an outer diameter smaller than that of the large-diameter portion 215) extending in the insertion direction ID of the insertion portion 21 and is integrally formed with the distal end of the large-diameter portion 215. The proximal-end side outer periphery of the small-diameter portion 216 is provided with a balloon attachment groove 2162 for attaching a balloon (not illustrated) that may swell and shrink and has the inside thereof filled with water. To attach the balloon, the ultrasound probe 211 is inserted into the balloon through the mouth portion (the mouth portion through which deaerated water is flown into the balloon) of the balloon. The mouth portion of the balloon is engaged with the balloon attachment groove 2161 and the balloon attachment groove 2162. In this state, the entire ultrasound probe 211 is covered with the balloon.

The small-diameter portion 216 is provided with a balloon water filling port 2163 for filling the inside of the balloon with a liquid. The balloon water filling port 2163 forms part of the distal-end side fourth conduit 64.

The small-diameter portion 216 is further provided with a balloon suction port 2164 for suctioning a liquid, or the like, inside the balloon. The balloon suction port 2164 forms part of the distal-end side fifth conduit 65.

Next, the configurations of the conduits 6 formed in the ultrasound endoscope 2 are described with reference to FIG. 3. FIG. 3 is a diagram schematically illustrating the conduits 6 provided in the ultrasound endoscope 2.

As described above, the distal-end side first to fifth conduits 61 to 65 and the proximal-end side first to third conduits 66 to 68 constitute the conduits 6.

The distal-end side first conduit 61 is a conduit for protruding a treatment instrument (e.g., a puncture needle) to the outside through the instrument channel 2154 and for suctioning a liquid inside the subject through the instrument channel 2154. As illustrated in FIG. 3, the distal-end side first conduit 61 includes a treatment instrument tube 611 and a suction tube 612.

The treatment instrument tube 611 extends inside the bent portion 213 and the flexible tube portion 214 and has one end thereof communicating with the instrument channel 2154. The treatment instrument tube 611 communicates with a treatment instrument insertion port 223 provided in the operating portion 22. Specifically, the treatment instrument (e.g., a puncture needle) is inserted into the treatment instrument tube 611 through the treatment instrument insertion port 223 and is protruded to the outside through the instrument channel 2154.

The suction tube 612 extends inside the operating portion 22 and has one end thereof communicating with the other end of the treatment instrument tube 611 and the other end thereof communicating with the suction cylinder 8.

The distal-end side second conduit 62 is a conduit for supplying air from the air/water supply hole 2155 toward the imaging hole (not illustrated), extending inside the bent portion 213, the flexible tube portion 214, and the operating portion 22, and having one end thereof communicating with the air/water supply hole 2155 and the other end thereof communicating with the air/water supply cylinder 7.

The distal-end side third conduit 63 is a conduit for supplying water from the air/water supply hole 2155 toward the imaging hole (not illustrated), extending inside the bent portion 213, the flexible tube portion 214, and the operating portion 22, and having one end thereof communicating with the air/water supply hole 2155 and the other end thereof communicating with the air/water supply cylinder 7.

The distal-end side fourth conduit 64 is a conduit for filling the inside of the balloon (not illustrated) with water through a water supply hole 217, extending inside the bent portion 213, the flexible tube portion 214, and the operating portion 22, and having one end thereof communicating with the balloon water filling port 2163 and the other end thereof communicating with the air/water supply cylinder 7.

The distal-end side fifth conduit 65 is a conduit for suctioning water inside the balloon (not illustrated) through the suction hole 218, extending inside the bent portion 213, the flexible tube portion 214, and the operating portion 22, and having one end thereof communicating with the balloon suction port 2164 and the other end thereof communicating with the suction cylinder 8.

The proximal-end side first conduit 66 is a conduit for allowing the air discharged from the light source pump P1 to flow into the air/water supply cylinder 7 and the water supply tank Ta and extending inside the operating portion 22, the universal cable 23, and the endoscope connector 24. The proximal-end side first conduit 66 branches into two in the endoscope connector 24 and has one end thereof communicating with the air supply ferrule 244 and the pressure ferrule 245 and the other end thereof communicating with the air/water supply cylinder 7.

The proximal-end side second conduit 67 is a conduit for allowing the water discharged from the water supply tank Ta to flow into the air/water supply cylinder 7 and extending inside the operating portion 22, the universal cable 23, and the endoscope connector 24. The proximal-end side second conduit 67 has one end thereof communicating with the water supply ferrule 246 and has the other end thereof communicating with the air/water supply cylinder 7.

The proximal-end side third conduit 68 is a conduit for suctioning a liquid inside the suction cylinder 8, extending inside the operating portion 22, the universal cable 23, and the endoscope connector 24, and having one end thereof communicating with the suction ferrule 247 and the other end thereof communicating with the suction cylinder 8.

Figure 6:
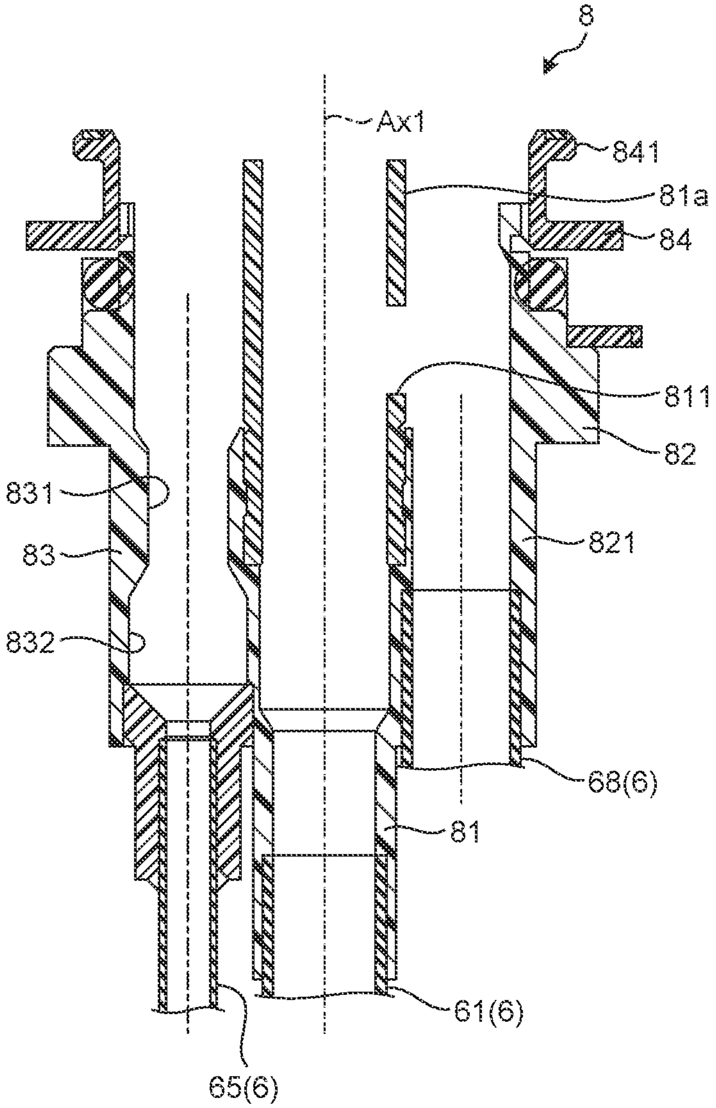
FIG. 6 is a cross-sectional view illustrating a configuration of a suction cylinder.

Next, the configuration of the suction cylinder 8 is described with reference to FIG. 6. FIG. 6 is a cross-sectional view illustrating the configuration of the suction cylinder 8. The suction cylinder 8 has a cylindrical shape having a central axis Ax1 extending in a vertical direction in FIG. 6 as a central axis. As illustrated in FIG. 6, the suction cylinder 8 includes, along the central axis Ax1, a first communicating conduit 81, a cylindrical portion 82 covering the outer periphery of the first communicating conduit 81, and a third communicating conduit 83 extending at a position away from the central axis Ax1 in a direction along the central axis Ax1.

At the upper end portion of the first communicating conduit 81, a first communicating pipe 81*a* having an inner diameter allowing a shaft 103 of the suction button 10, described below, to be slidably engaged is coaxially and integrally connected to the first communicating conduit 81. The first communicating pipe 81*a* is provided with a communicating hole 811 that communicates with the cylindrical portion 82. As illustrated in FIG. 6, the lower end portion of the first communicating conduit 81 is coupled to the other end of the distal-end side first conduit 61 via a ferrule, or the like.

As illustrated in FIG. 6, a second communicating conduit 821 is formed in part of the bottom surface of the cylindrical portion 82, and the second communicating conduit 821 is coupled to the other end of the proximal-end side third conduit 68. As illustrated in FIG. 6, a ferrule portion 84 for attaching the suction button 10 is secured to the upper end of the cylindrical portion 82.

The third communicating conduit 83 includes, sequentially from the upper side, a small-diameter portion 831 and a large-diameter portion 832. As illustrated in FIG. 6, the third communicating conduit 83 is coupled to the other end of the distal-end side fifth conduit 65 via a ferrule, or the like.

The ferrule portion 84 has a cylindrical shape and is secured to the outer peripheral surface of the cylindrical portion 82 by, for example, screwing. The ferrule portion 84 protrudes from the inside of the operating portion 22 to the outside in a state where the ferrule portion 84 is secured to the outer peripheral surface of the cylindrical portion 82. As illustrated in FIG. 6, the outer peripheral surface of the ferrule portion 84 is provided with an engagement protrusion 841 that has an annular shape extending over the entire outer peripheral surface and protrudes from the upper end of the outer peripheral surface to the side away from the central axis Ax1.

Figure 7:
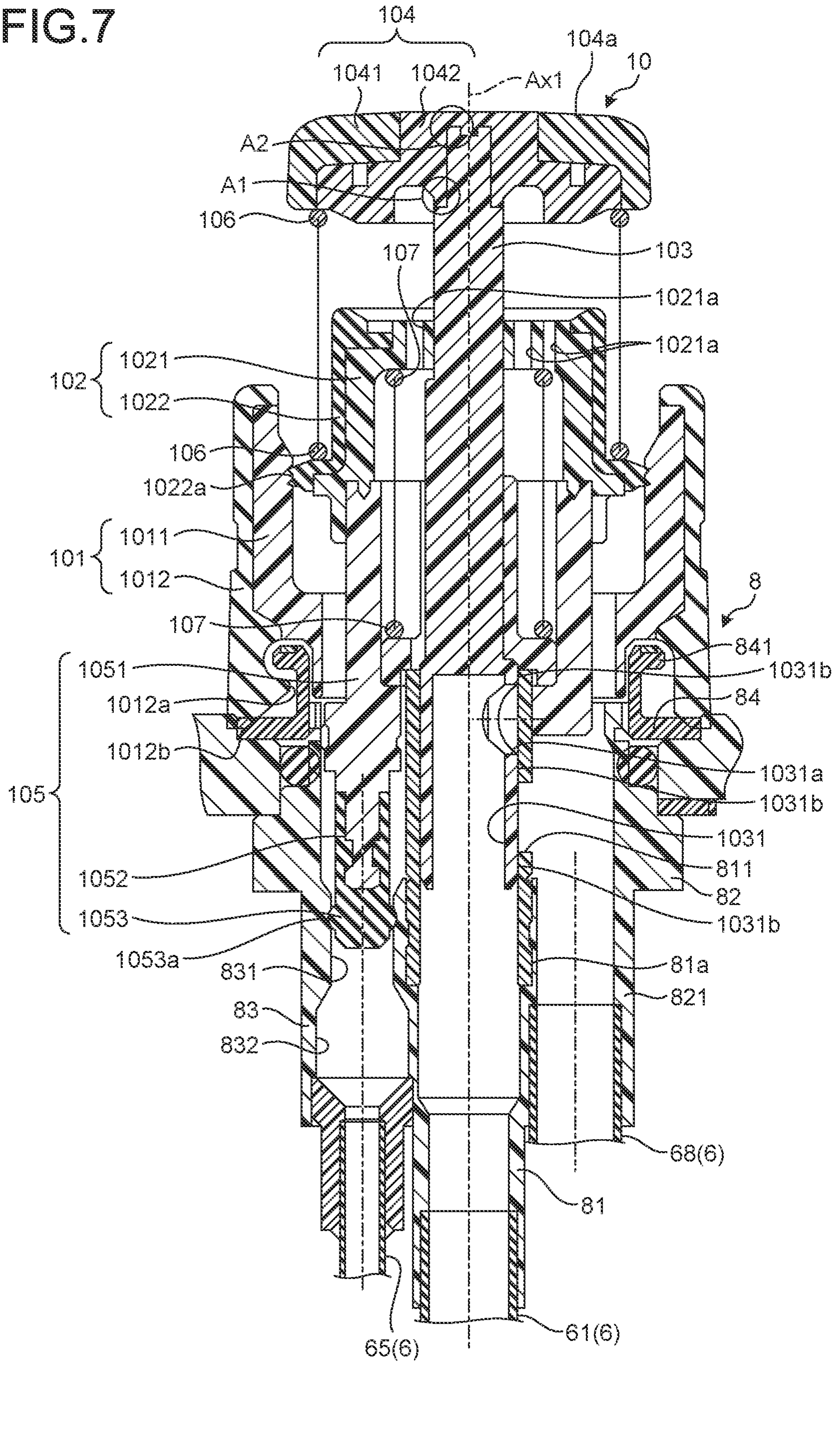
FIG. 7 is a cross-sectional view illustrating a state where a suction button is attached to the suction cylinder.
Figure 8:
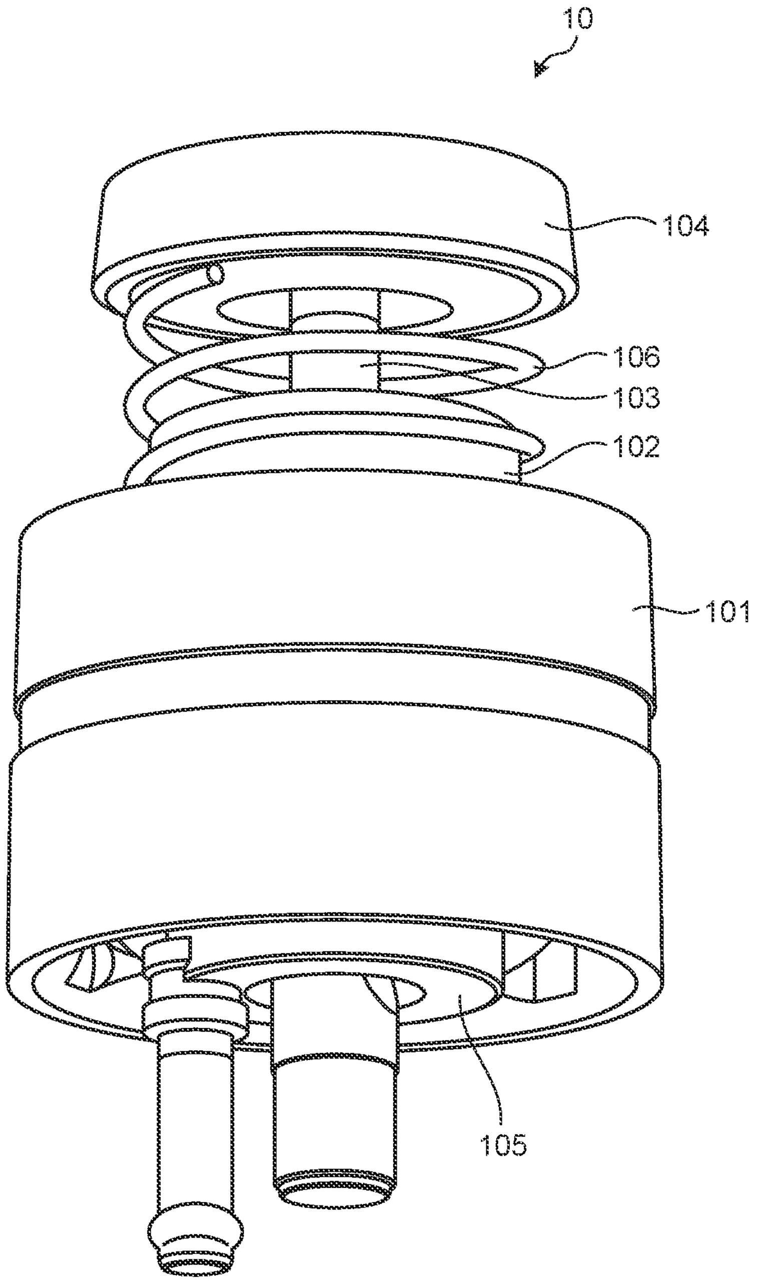
FIG. 8 is a perspective view illustrating the configuration of the suction button.
Figure 9:
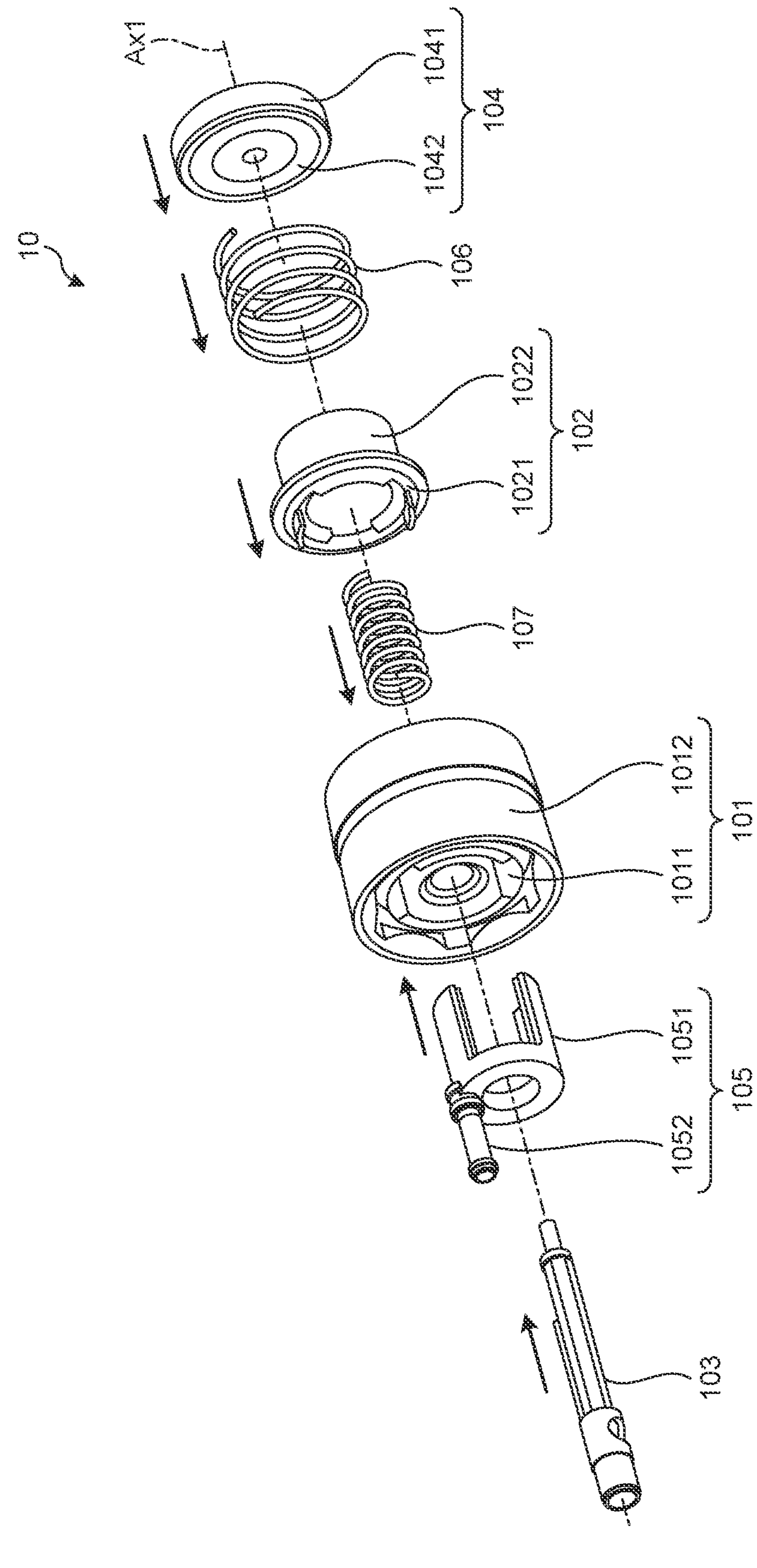
FIG. 9 is a perspective exploded view of the suction button.

Next, the configuration of the suction button 10 is described with reference to FIGS. 7 to 9. FIG. 7 is a cross-sectional view illustrating a state where the suction button 10 is attached to the suction cylinder 8. Specifically, FIG. 7 is a cross-sectional view illustrating a state where the suction button 10 is attached to the ferrule portion 84 (the suction cylinder 8). That is, in FIG. 7, the lower side indicates the distal end side in the attachment direction of the suction button 10 to the ferrule portion 84. FIG. 8 is a perspective view illustrating the configuration of the suction button 10. FIG. 9 is a perspective exploded view of the suction button 10.

The suction button 10 includes: an attachment 101 attached to the ferrule portion 84 (the suction cylinder 8); a movable spring bearing 102 movably held by the attachment 101; the shaft 103 movably held by the movable spring bearing 102; a cap 104 secured to one end of the shaft 103; a movable piston 105 secured to the movable spring bearing 102; a first coil spring 106 biasing the movable spring bearing 102 and the cap 104 in a direction apart from each other; and a second coil spring 107 biasing the attachment 101 and the movable spring bearing 102 (the movable piston 105) in a direction apart from each other. It is assumed that the suction button 10 is replaceable in the ultrasound endoscope 2 and the suction button 10 is disposable.

The attachment 101 includes: a cylindrical attachment main body 1011 made of rigid resin; and an attachment rubber 1012 that is made of an elastic material such as rubber, silicone, or thermoplastic elastomer, and covers the outer periphery of the attachment main body 1011. An end of the attachment rubber 1012 is provided with a claw-shaped attachment securing portion 1012*a*. When the attachment securing portion 1012*a* is engaged with the engagement protrusion 841 of the ferrule portion 84, the attachment 101 is secured to the ferrule portion 84. Further, an end of the attachment rubber 1012 is provided with a sealing portion 1012*b* that abuts the ferrule portion 84 so as to seal the gap between the attachment rubber 1012 and the ferrule portion 84.

The movable spring bearing 102 is joined to the movable piston 105 by ultrasound welding with part of the attachment 101 and the second coil spring 107 interposed therebetween. The movable spring bearing 102 includes: a cylindrical movable spring bearing main body 1021 made of rigid resin; and a movable spring bearing packing 1022 that is made of an elastic material such as rubber, silicone, or thermoplastic elastomer, and covers the outer periphery of the movable spring bearing main body 1021. The movable spring bearing packing 1022 is provided with a sealing portion 1022*a* to slidably seal the gap between the attachment main body 1011 and the movable spring bearing packing 1022.

As illustrated in FIG. 9, the shaft 103 is made of rigid resin and extends in substantially a rod-like shape. One end of the shaft 103 is inserted into the cap 104, and the other end thereof is inserted into the conduit (the first communicating conduit 81) of the ultrasound endoscope 2. The shaft 103 is moved inside the conduit (the first communicating conduit 81) to switch between suction conduits of the ultrasound endoscope 2. The shaft 103 is provided with a hole portion 1031 forming a hollow space extending in the direction of the central axis Ax1. As illustrated in FIG. 7, the hole portion 1031 extends from one end of the shaft 103 in the central axis Ax1, and the other end thereof is located within the shaft 103. The center axis Ax1 passes through the hole portion 1031. The shaft 103 is provided with a side surface along a direction perpendicular to the central axis Ax1 and a communicating hole 1031*a* communicating in the middle of the shaft 103 and the hole portion 1031. The outer peripheral surface of the hole portion 1031 is provided with a sealing portion 1031*b* to be slidably engaged with the inner peripheral surface of the first communicating pipe 81*a* and to seal the gap between the first communicating pipe 81*a* and the hole portion 1031 by engagement. The shaft 103 is joined to the cap 104 by ultrasound welding with part of the movable spring bearing 102 and the first coil spring 106 interposed therebetween.

The cap 104 receives the operation for moving the movable spring bearing 102 and the movable piston 105. A first member 1041 shaped like a hollow circular disk and a second member 1042 provided inside the first member 1041 are provided. The first member 1041 and the second member 1042 are made of rigid resin. A pressing surface 104*a*, which is pressed by the operator, is formed on one surface (the upper surface in FIG. 6) in a state where the first member 1041 and the second member 1042 are engaged with each other. A shaft hole 1042*a* is formed on the surface of the second member 1042 on the side opposite to the pressing surface 104*a*. The second member 1042 includes a tubular rib 1042*b* disposed on the outer periphery of the shaft hole 1042*a*. The cap 104 is joined to the shaft 103 by ultrasound welding.

The movable piston 105 is movable so as to be insertable into or removable from the conduit (the third communicating conduit 83) of the ultrasound endoscope 2. The movable piston 105 switches between suction conduits of the ultrasound endoscope 2 in accordance with the insertion into or removal from the conduit (the third communicating conduit 83).

The movable piston 105 includes: a movable piston main body 1051 secured to the movable spring bearing 102; a piston portion 1052 extending along the conduit (the third communicating conduit 83); and a packing portion 1053 disposed on the outer periphery of the piston portion 1052 to fill the gap between the conduit (the third communicating conduit 83) and the piston portion 1052 inserted into the conduit (the third communicating conduit 83). The movable piston main body 1051 and the piston portion 1052 are integrally formed and are made of rigid resin. The piston portion 1052 extends at a position different from the center of the cap 104. The packing portion 1053 is made of an elastic material, such as rubber, silicone, or thermoplastic elastomer, and is provided with a sealing portion 1053*a* to slidably seal the gap between the small-diameter portion 831 of the third communicating conduit 83 and the packing portion 1053.

The first coil spring 106 is formed by winding a wire rod in a spiral manner. The first coil spring 106 has one end thereof abutting the movable spring bearing 102 and the other end thereof abutting the cap 104 so as to apply a biasing force in a direction away from each other. The biasing force of the first coil spring 106 is received by the abutting surface between the shaft 103 and the attachment 101.

The second coil spring 107 is formed by winding a wire rod in a spiral manner. The second coil spring 107 has one end thereof abutting the attachment 101 and the other end thereof abutting the movable spring bearing 102 so as to apply a biasing force in a direction away from each other. The biasing force by the second coil spring 107 is received by the abutting surface between the attachment 101 and the movable piston 105. The amount of power of the second coil spring 107 while in use is higher than the maximum amount of power of the first coil spring 106 while in use.

In the suction button 10, when the shaft 103 moves relative to the movable spring bearing 102 in accordance with the operation on the cap 104, the second communicating conduit 821 of the ultrasound endoscope 2 communicates with the first communicating conduit 81. In the suction button 10, when the movable piston 105 moves together with the movable spring bearing 102 relative to the attachment 101 in accordance with the operation on the cap 104, the third communicating conduit 83 of the ultrasound endoscope 2 communicates with the second communicating conduit 821. The operation of the suction button 10 is described below in more detail.

Next, the assembly of the suction button 10 is described. The movable piston 105 is engaged with the attachment 101 from below (the left side along the central axis Ax1 in FIG. 9). The attachment 101 and the movable piston 105 are secured to each other so as not to rotate relatively around the central axis Ax1 as a rotation axis. Subsequently, the movable spring bearing 102 is attached to the attachment 101 from above (the right side along the central axis Ax1 in FIG. 9) with the second coil spring 107 interposed therebetween. The movable spring bearing 102 and the movable piston 105 are secured to each other by ultrasound welding.

Then, the shaft 103 is inserted into the movable piston 105, which is integrated with the attachment 101, etc., from below. Here, the attachment 101 and the shaft 103 are secured to each other so as not to rotate relatively around the central axis Ax1 as a rotation axis. Subsequently, the cap 104 is attached to the attachment 101 from above with the first coil spring 106 interposed therebetween. Here, the shaft 103 and the cap 104 are secured to each other by ultrasound welding. Thus, the above-described suction button 10 is obtained.

Next, the connection states of the conduits 6 by using the air/water supply button 9 and the suction button 10 are described with reference to FIGS. 7 and 10 to 15. In the following description, the case of no operation, the case of closing a leak hole 91 of the air/water supply button 9 with the finger, the case of a one-step pressing operation, and the case of a two-step pressing operation are sequentially described.

[Case of No Operation]

Figure 10:
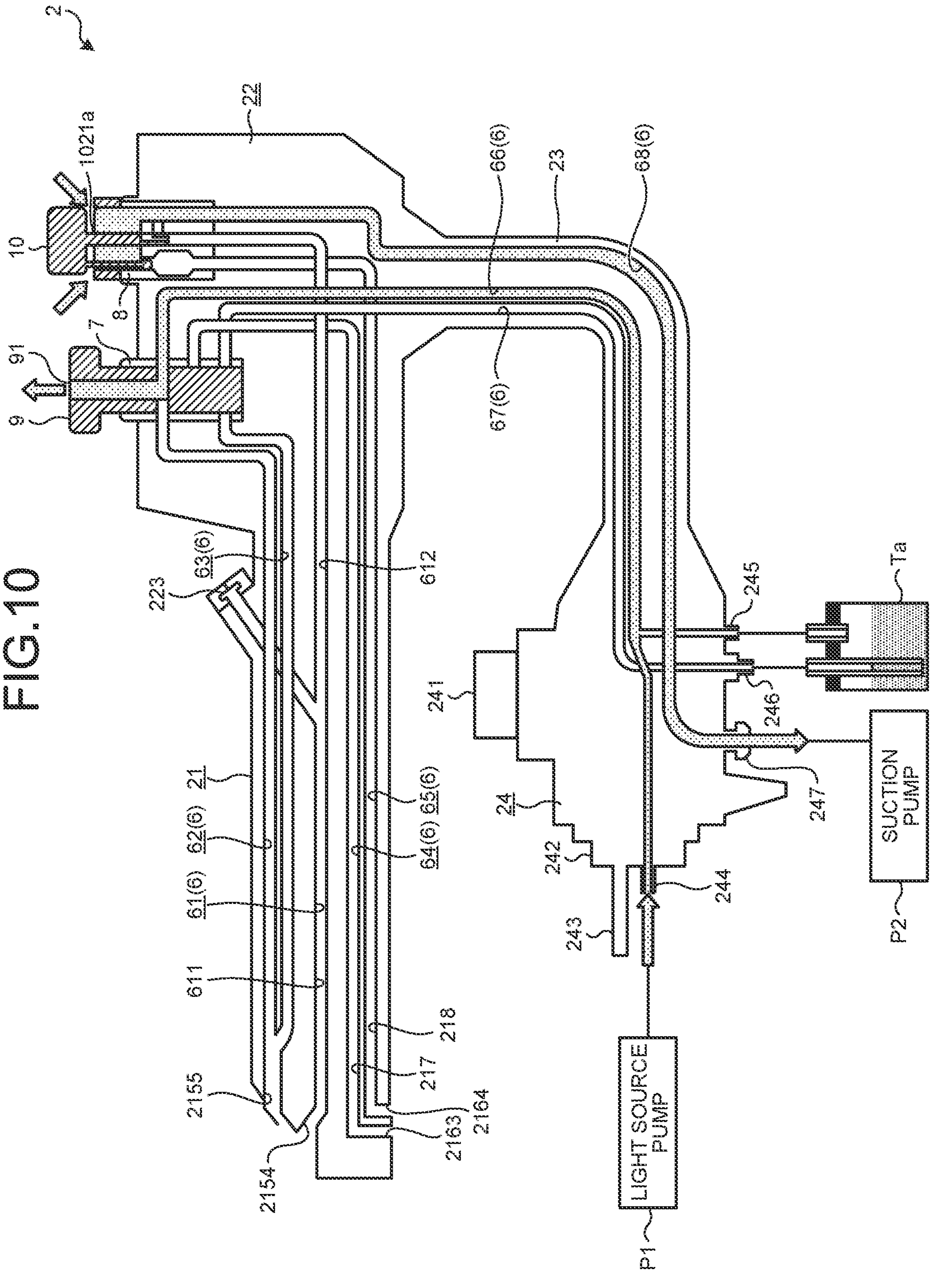
FIG. 10 is a diagram illustrating connection states of the conduits is a case where no operation is performed on an air/water supply button and the suction button.

FIGS. 7 and 10 are diagrams illustrating the connection states of the conduits in a case where no operation is performed on the air/water supply button and the suction button.

In a case where no operation is performed on the air/water supply button 9, the air discharged from the light source pump P1 flows toward the air/water supply cylinder 7 via the proximal-end side first conduit 66. Then, the air flowing toward the air/water supply cylinder 7 passes through the leak hole 91 to be discharged to the outside of the ultrasound endoscope 2.

In a case where no operation is performed on the suction button 10, the distal-end side first conduit 61 is sealed with the sealing portion 1031*b*, and the distal-end side fifth conduit 65 is sealed with the sealing portion 1053*a*. Although the outside air is blocked by the sealing portions 1012*b* and 1022*a*, only a leak hole 1021*a* is open. Therefore, in accordance with the drive of the suction pump P2, the air outside the ultrasound endoscope 2 flows into the suction cylinder 8 via the leak hole 1021*a* of the suction button 10 to be suctioned by the suction pump P2 via the proximal-end side third conduit 68. As the hole area of the leak hole 1021*a* is more than the cross-sectional area of the proximal-end side third conduit 68, the suction pressure by the suction pump P2 is prevented from acting on the distal-end side first conduit 61 and the distal-end side fifth conduit 65.

That is, in the case of no operation, the distal-end side first to fifth conduits 61 to 65 are not connected to the proximal-end side first to third conduits 66 to 68, and therefore the air supply, the water supply, or the suction are not performed through the distal end of the insertion portion 21.

[Case of Closing the Leak Hole with the Finger]

Figure 11:
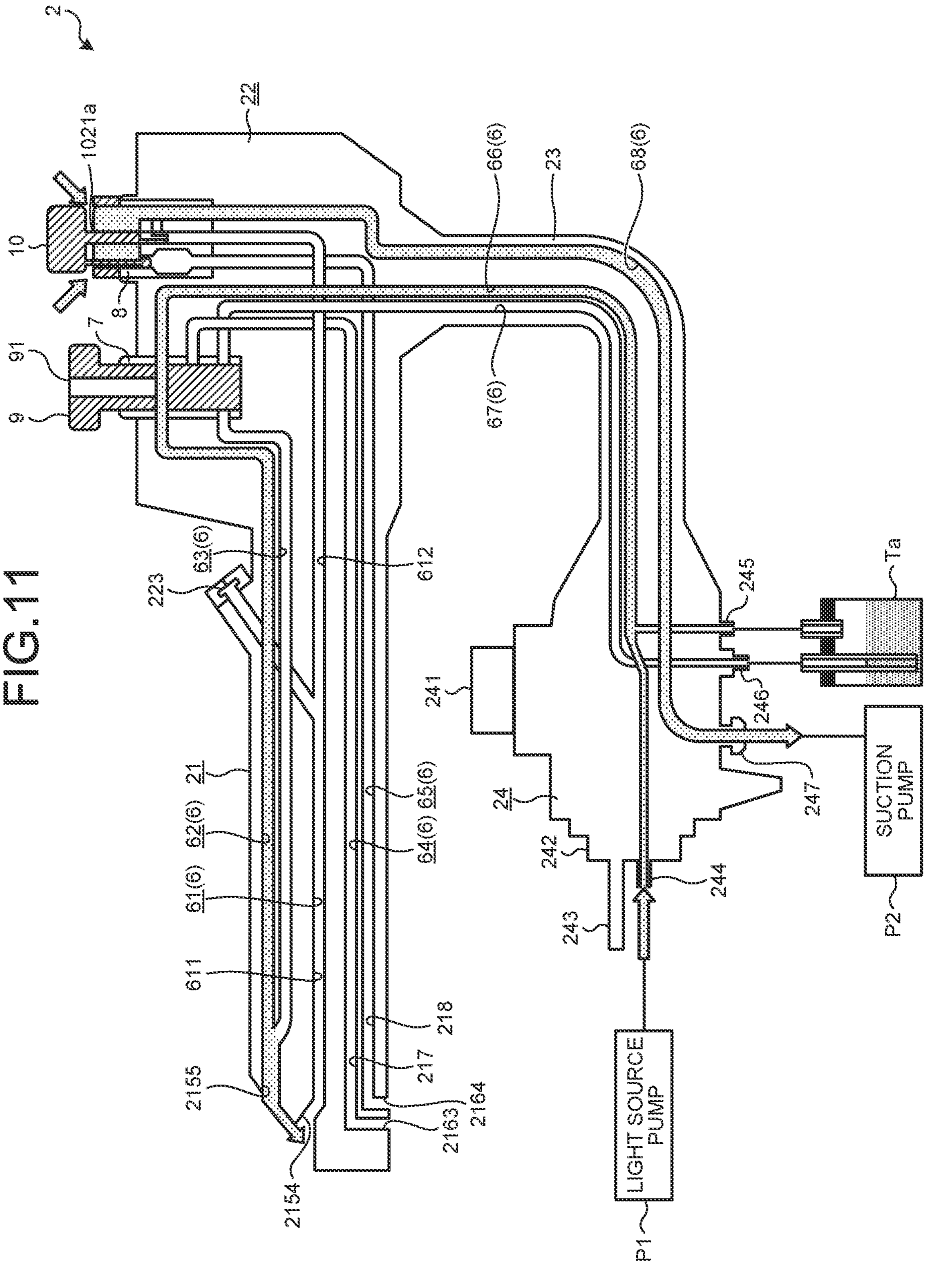
FIG. 11 is a diagram illustrating the connection states of the conduits when a leak hole of the air/water supply button is closed with a finger.

FIG. 11 is a diagram illustrating the connection states of the conduits 6 when the leak hole 91 of the air/water supply button 9 is closed with the finger. In FIG. 11, as is the case with FIG. 10, no operation is performed on the suction button 10.

In a case where the leak hole 91 is closed with the finger, the air flowing into the air/water supply cylinder 7 flows through the distal-end side second conduit 62. Then, as illustrated in FIG. 11, the air flowing through the distal-end side second conduit 62 is discharged from the air/water supply hole 2155 toward the objective optical system (not illustrated) in the imaging hole (not illustrated).

[Case of One-step Pressing Operation]

Figure 12:
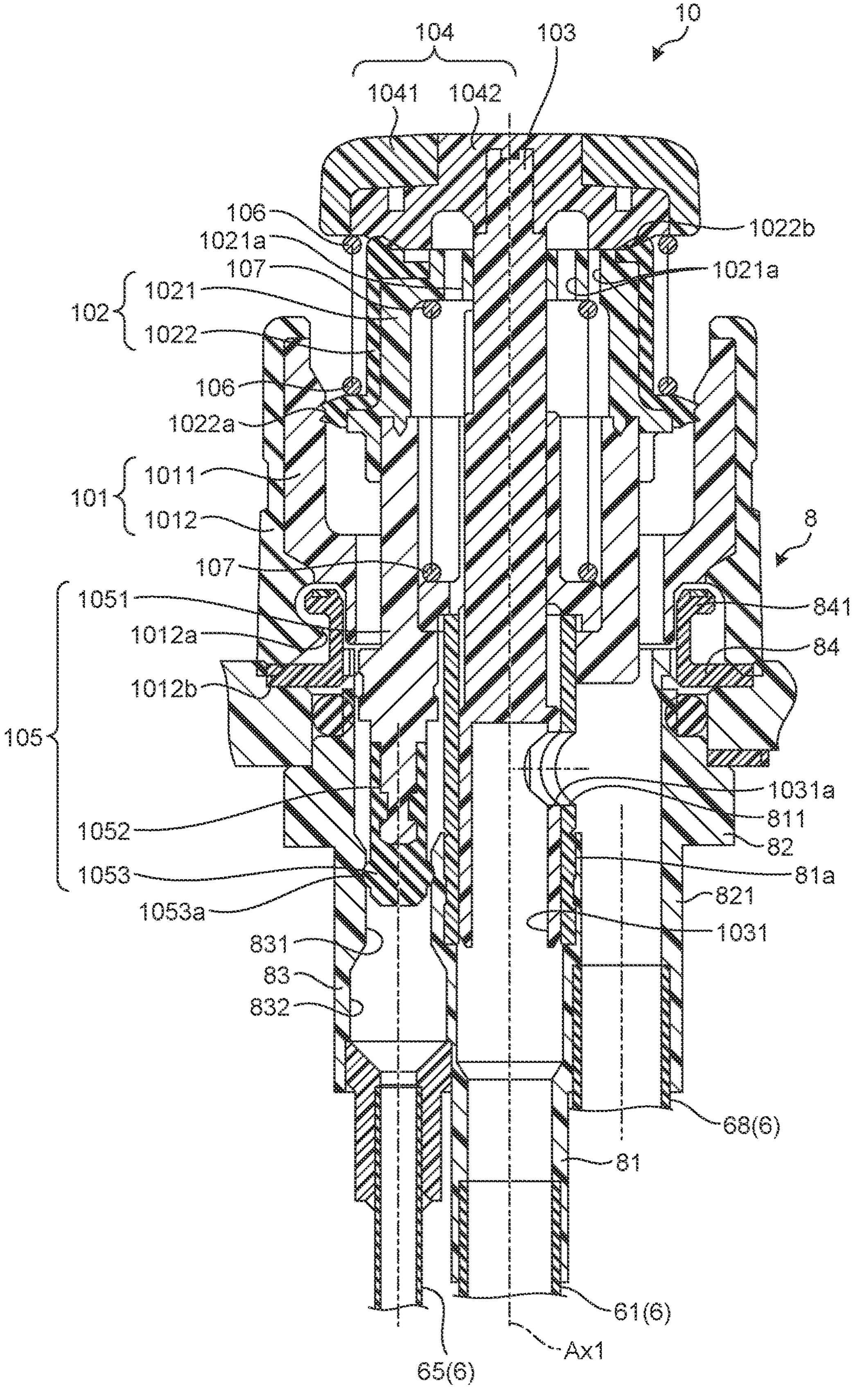
FIG. 12 is a cross-sectional view illustrating a state where a one-step pressing operation is performed on the suction button.
Figure 13:
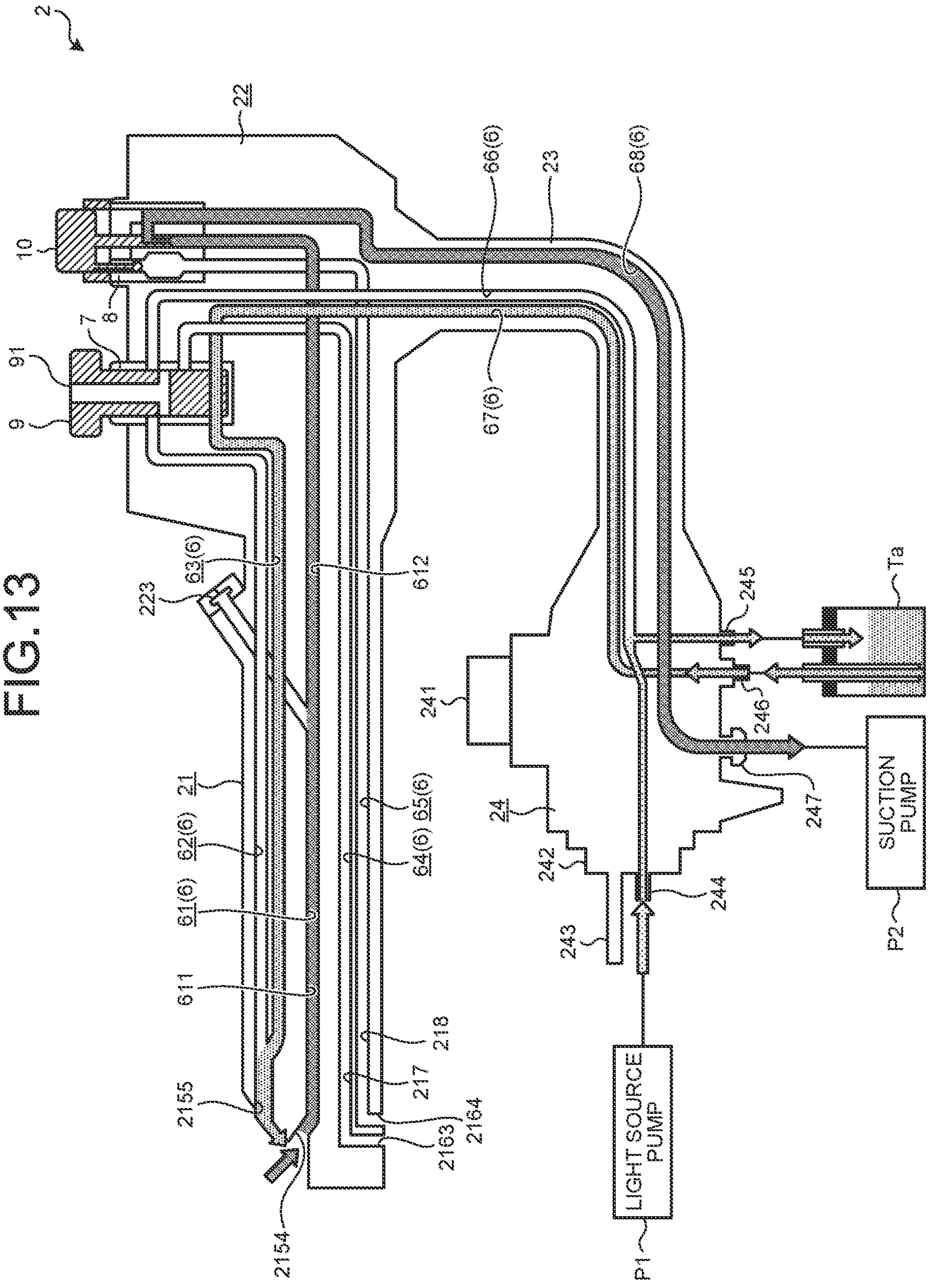
FIG. 13 is a diagram illustrating the connection states of the conduits in a case where a one-step pressing operation is performed on the air/water supply button and the suction button.

FIG. 12 is a cross-sectional view illustrating a state where a one-step pressing operation is performed on the suction button 10. FIG. 13 is a diagram illustrating the connection states of the conduits 6 in a case where a one-step pressing operation is performed on the air/water supply button 9 and the suction button 10.

In a case where a one-step pressing operation is performed on the air/water supply button 9, the air discharged from the light source pump P1 flows into the water supply tank Ta via the proximal-end side first conduit 66 to apply pressure to the inside of the water supply tank Ta so that the water flows from the water supply tank Ta, as illustrated in FIG. 13. Then, the water from the water supply tank Ta flows toward the air/water supply cylinder 7 via the proximal-end side second conduit 67. The water flowing toward the air/water supply cylinder 7 flows through the distal-end side third conduit 63. Then, the water flowing through the distal-end side third conduit 63 is discharged from the air/water supply hole 2155 toward the objective optical system (not illustrated) in the imaging hole (not illustrated).

In a case where a one-step pressing operation is performed on the suction button 10, the cap 104 abuts the movable spring bearing packing 1022 of the movable spring bearing 102, and the sealing portion 1022*b* seals the leak hole 1021*a,* as illustrated in FIG. 12. The shaft 103, which is integrated with the cap 104 by ultrasound welding, also slides downward in the first communicating pipe 81*a* so that the communicating hole 1031*a* of the shaft 103 becomes coaxial with the communicating hole 811 of the first communicating pipe 81*a*. Here, the distal-end side fifth conduit 65 is sealed by the sealing portion 1053*a,* and the outside air is blocked by the sealing portions 1012*b,* 1022*a*, and 1022*b*. Furthermore, as the communicating hole 1031*a* of the shaft 103 is coaxial (has an opening) with the communicating hole 811 of the first communicating pipe 81*a*, the distal-end side first conduit 61 connects (communicates) with the proximal-end side third conduit 68. A liquid inside the subject flows into the distal-end side first conduit 61 through the instrument channel 2154 to be suctioned by the suction pump P2 via the suction cylinder 8 and the proximal-end side third conduit 68. To suction a liquid inside the subject through the instrument channel 2154 as described above, a forceps cover (not illustrated) is attached to the treatment instrument insertion port 223 so as to close the treatment instrument insertion port 223 and cause the suction pressure to be applied to the distal end side (the side of the instrument channel 2154).

[Case of Two-Step Pressing Operation]

Figure 14:
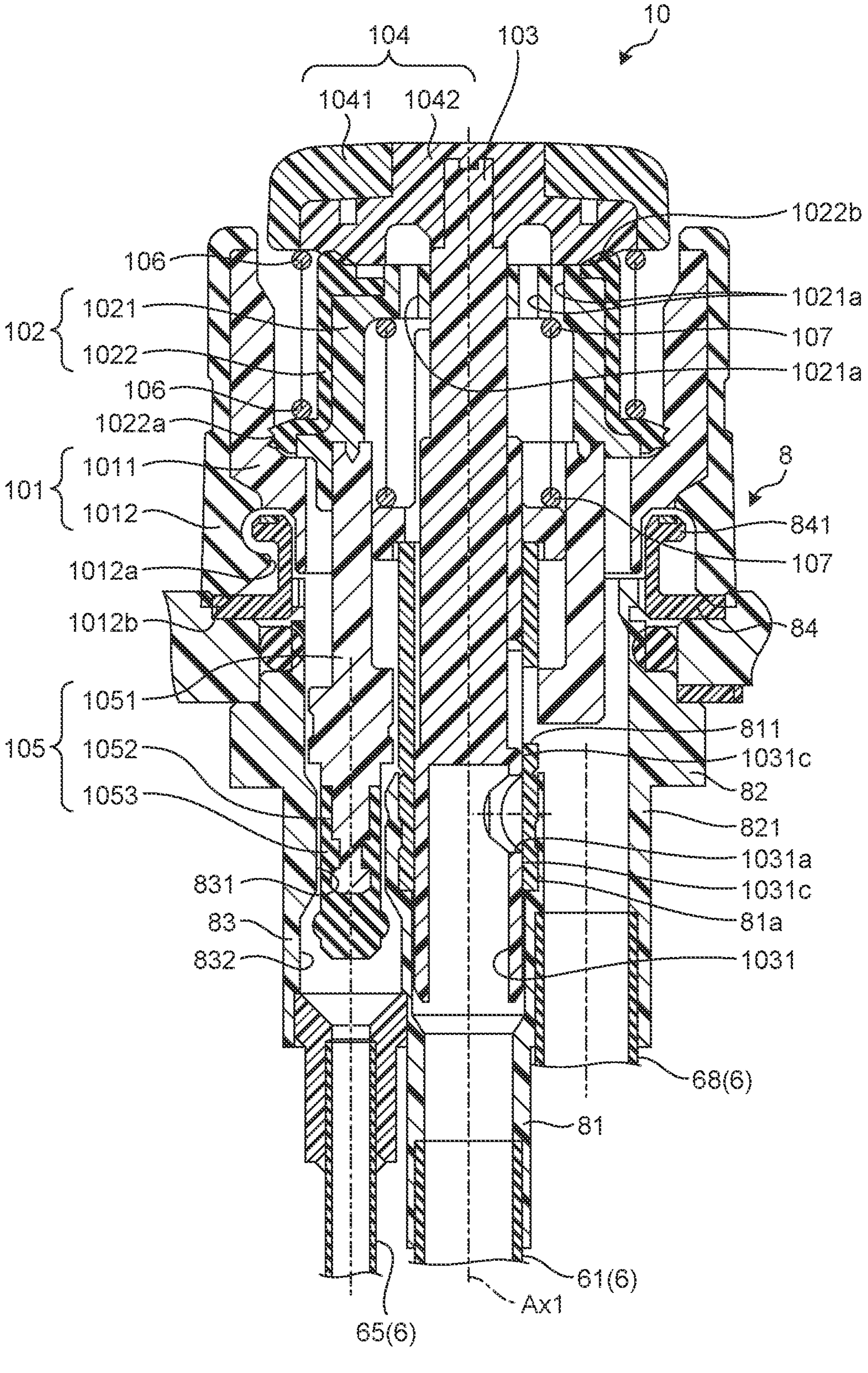
FIG. 14 is a cross-sectional view illustrating a state where a two-step pressing operation is performed on the suction button.
Figure 15:
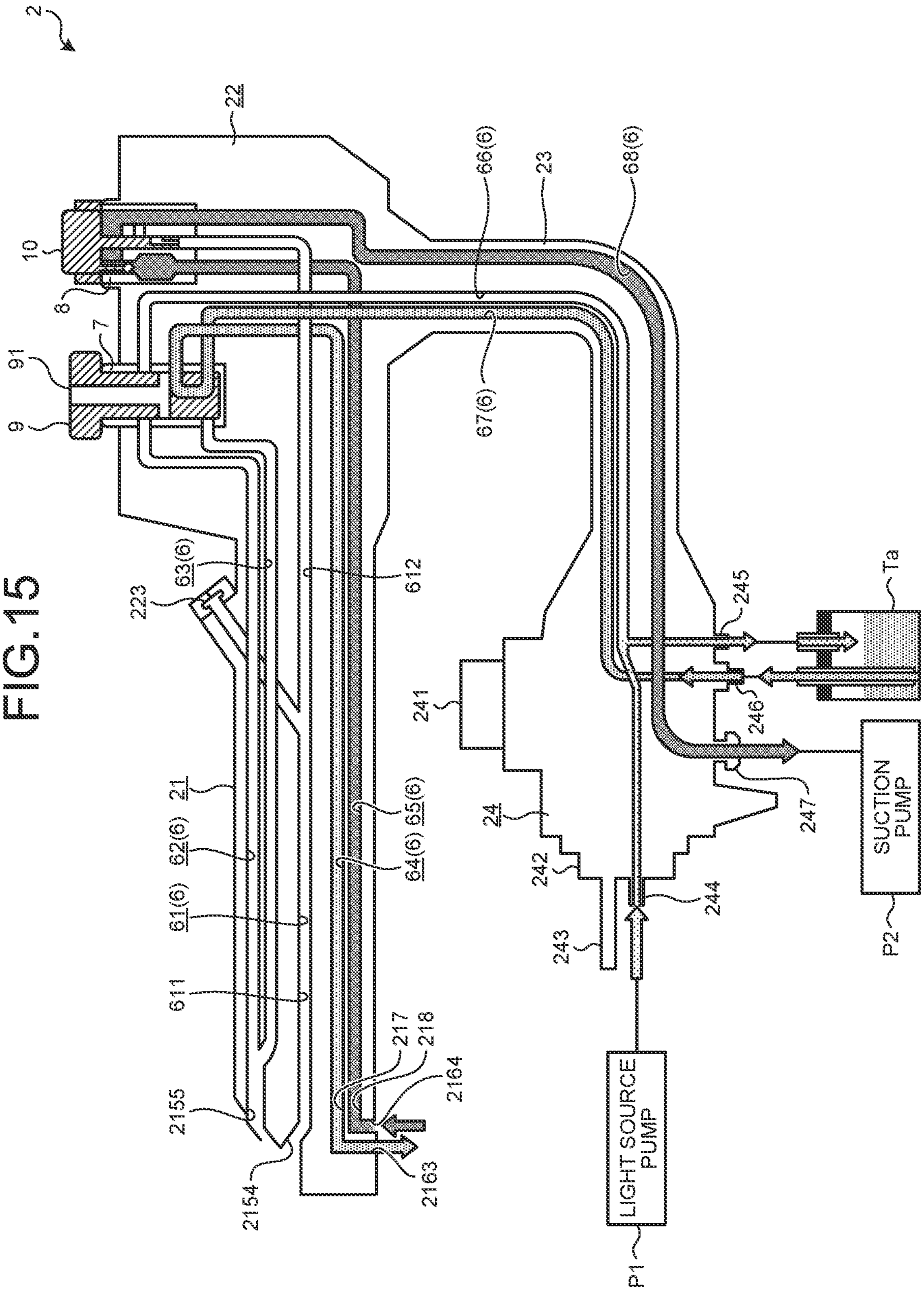
FIG. 15 is a diagram illustrating the connection states of the conduits in a case where a two-step pressing operation is performed on the air/water supply button and the suction button.

FIG. 14 is a cross-sectional view illustrating a state where a two-step pressing operation is performed on the suction button 10. FIG. 15 is a diagram illustrating the connection states of the conduits 6 in a case where a two-step pressing operation is performed on the air/water supply button 9 and the suction button 10.

In a case where a two-step pressing operation is performed on the air/water supply button 9 (in a case where a one-step pressing operation is further performed in the state illustrated in FIG. 13), the water flowing toward the air/water supply cylinder 7 flows into the distal-end side fourth conduit 64. Then, as illustrated in FIG. 15, the water flowing through the distal-end side fourth conduit 64 passes through the water supply hole 217 and the balloon water filling port 2163 to fill the balloon (not illustrated).

In a case where a two-step pressing operation is performed on the suction button 10, as illustrated in FIG. 14, while the sealing between the cap 104 and the movable spring bearing 102 by the sealing portion 1022*b* and the sealing between the movable spring bearing 102 and the attachment 101 by the sealing portion 1022*a* are maintained, the shaft 103 and the movable piston 105 move downward in the first communicating pipe 81*a* and the third communicating conduit 83, respectively, a sealing portion 1031*c* seals the gap between the shaft 103 and the first communicating pipe 81*a* due to the slidable engagement between the shaft 103 and the first communicating pipe 81*a*, and the packing portion 1053 of the movable piston 105 is located between the small-diameter portion 831 and the large-diameter portion 832 of the third communicating conduit 83. Here, the distal-end side first conduit 61 is sealed by the sealing portion 1031*c,* and the outside air is blocked by the sealing portions 1012*b,* 1022*a,* and 1022*b*. When the packing portion 1053 of the movable piston 105 moves to the large-diameter portion 832 of the third communicating conduit 83, the sealing portion 1053*a* is released so that the distal-end side fifth conduit 65 connects (communicates) with the proximal-end side third conduit 68. Then, a liquid (e.g., water in the balloon) inside the subject flows into the distal-end side fifth conduit 65 through the balloon suction port 2164 to be suctioned by the suction pump P2 via the suction cylinder 8 and the proximal-end side third conduit 68.

Figure 16B:
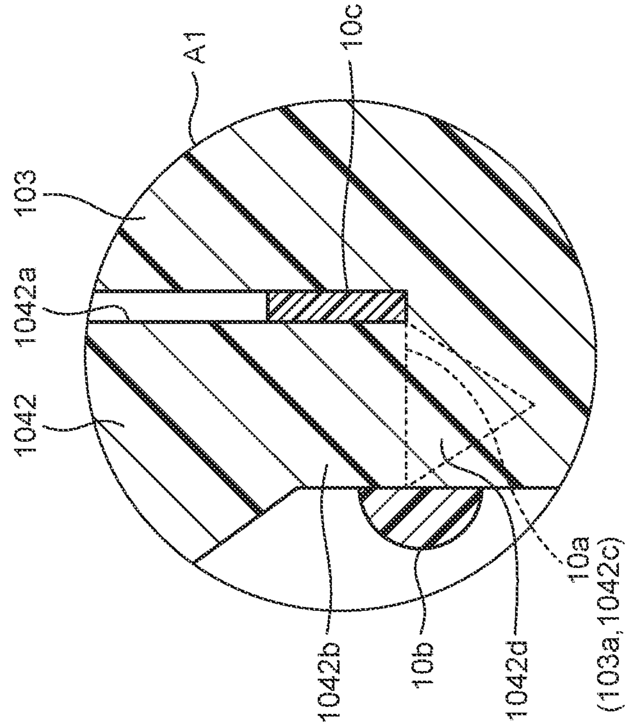
FIGS. 16A and 16B are a partially enlarged view of a region A1 in FIG. 7.
Figure 16A:
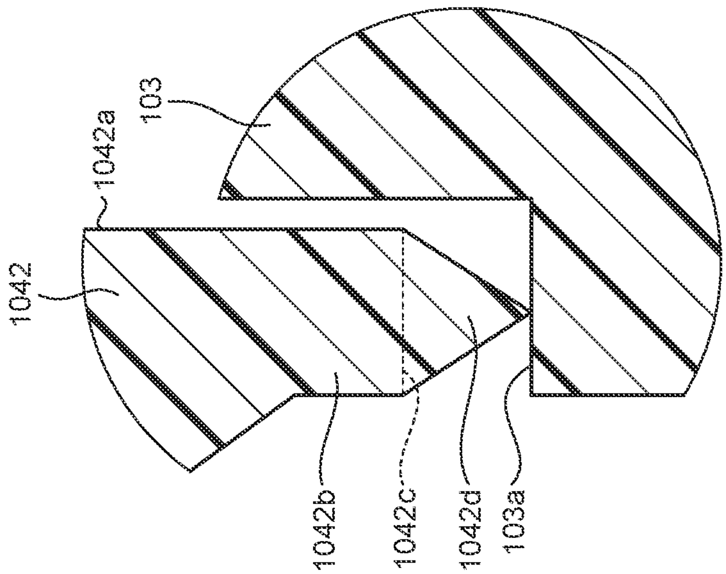

Next, a joint portion between the shaft 103 and the cap 104 is described. FIGS. 16A and 16B are a partially enlarged view of a region A1 in FIG. 7; FIG. 16A illustrates the region A1 before welding, and FIG. 16B illustrates the region A1 after welding. As illustrated in FIGS. 16A and 16B, a first welded portion (welded surface) 10*a* is disposed on an abutting surface 103*a* of the shaft 103 where the rib 1042*b* abuts, and in this portion, a melted portion end 1042*c* of the second member 1042, which is melted by ultrasound vibration of the cap 104, is joined with an extreme surface portion of the shaft 103. Melted resin 1042*d* of the second member 1042, which is melted by ultrasound vibration, flows out separately as resin 10*b* and resin 10*c* to the outer peripheral side and the inner peripheral side of the first welded portion (the welded surface) 10*a* so as to cover and reinforce the joint portion between the second member 1042 and the shaft 103 like an adhesive. Particularly, as the resin 10*c* acts as a force in the shearing direction against the force in the pulling direction of the cap 104 with respect to the shaft 103, the adhesive strength is increased.

Figure 17B:
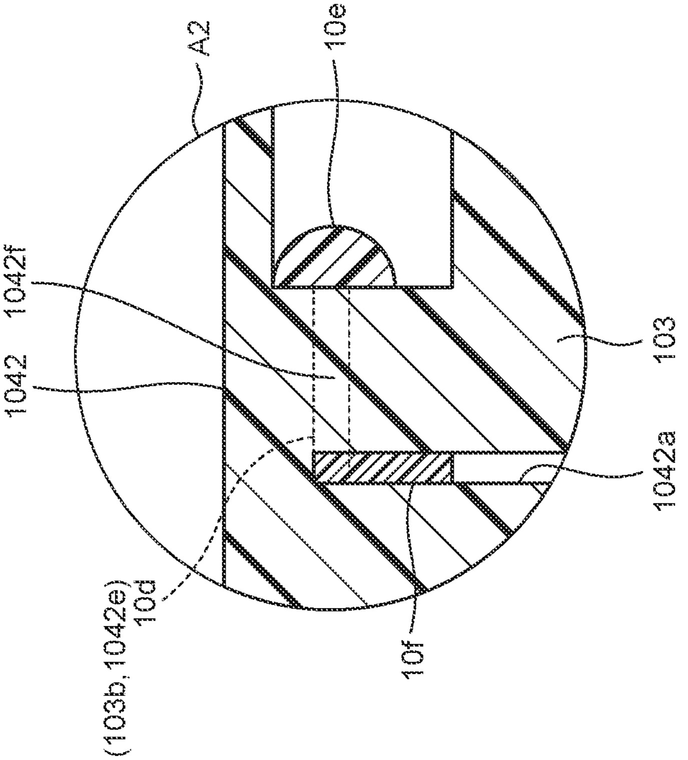
FIGS. 17A and 17B are a partially enlarged view of a region A2 in FIG. 7.
Figure 17A:
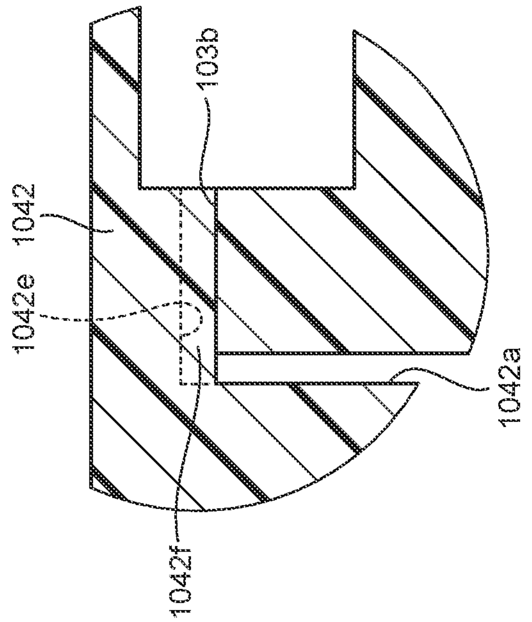

FIGS. 17A and 17B are a partially enlarged view of a region A2 in FIG. 7; FIG. 17A illustrates the region A2 before welding, and FIG. 17B illustrates the region A2 after welding. As illustrated in FIGS. 17A and 17B, a second welded portion (welded surface) 10*d* is disposed on a distal end 103*b* of the shaft 103, and in this portion, a melted portion end 1042*e* of the second member 1042, which is melted by ultrasound vibration of the cap 104, is joined with an extreme surface portion at the distal end of the shaft 103. Melted resin 1042*f* of the second member 1042, which is melted by ultrasound vibration, flows out separately as resin 10*e* and resin 10*f* to the outer peripheral side and the inner peripheral side of the second welded portion (the welded surface) 10*d* so as to cover and reinforce the joint portion between the second member 1042 and the shaft 103 like an adhesive. Particularly, as the resin 10*f* acts as a force in the shearing direction against the force in the pulling direction of the cap 104 with respect to the shaft 103, the adhesive strength is increased.

As described in FIGS. 7, 16A, 16B, 17A, and 17B, the first welded portion 10*a* and the second welded portion 10*d* are spaced apart from each other along the direction in which the shaft 103 extends. It is preferable that the first welded portion 10*a* and the second welded portion 10*d* are spaced apart from each other by more than half of the radius of the circular pressing surface 104*a* of the cap 104 along the direction in which the shaft 103 extends. As a result, even when the position near the outer periphery of the circular pressing surface 104*a* is pressed and a force is applied in such a direction to incline the cap 104 with respect to the central axis Ax1, the cap 104 and the shaft 103 are prevented from being separated from each other as the cap 104 and the shaft 103 are joined to each other at two positions (the first welded portion 10*a* and the second welded portion 10*d*) along the direction in which the shaft 103 extends.

Figure 18:
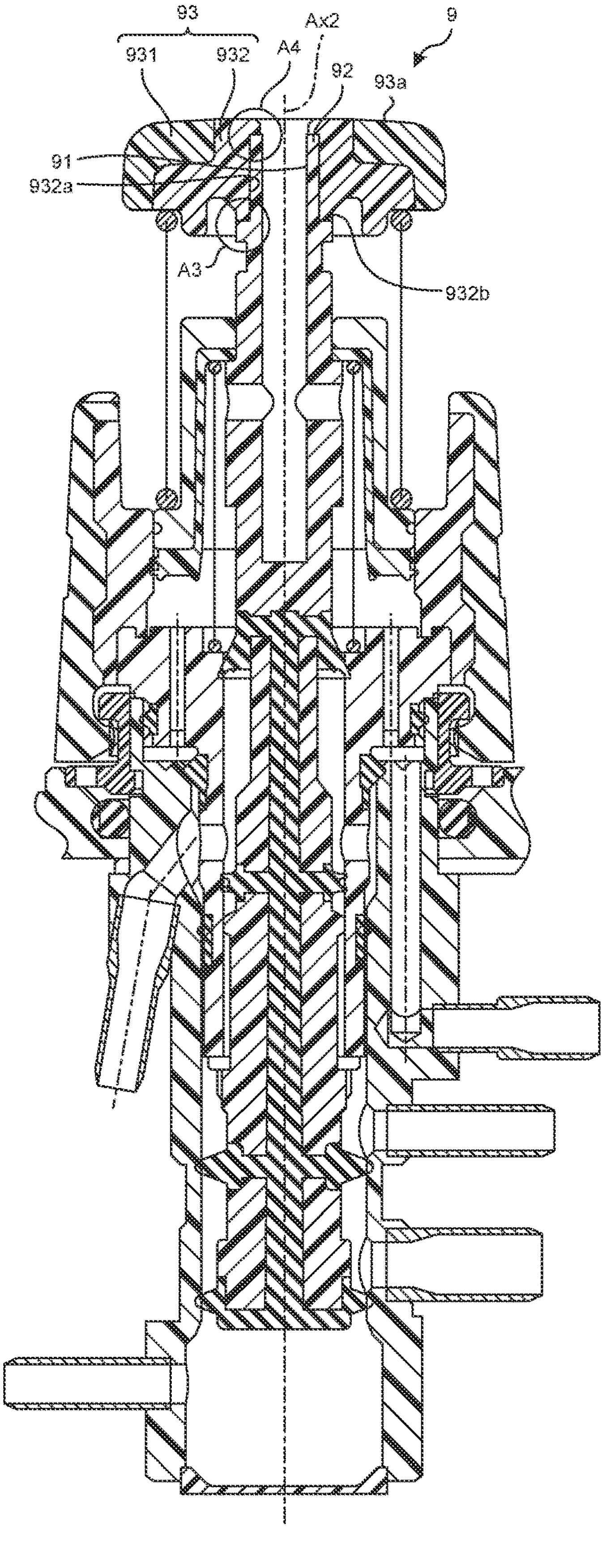
FIG. 18 is a cross-sectional view illustrating a state where the air/water supply button is attached to an air/water supply cylinder.

The identical configuration may be applied to the air/water supply button 9. FIG. 18 is a cross-sectional view illustrating a state where the air/water supply button is attached to the air/water supply cylinder. As illustrated in FIG. 18, the air/water supply button 9 includes a shaft 92 provided with a leak hole 91 and a cap 93 including a pressing surface 93*a* to be pressed by the operator.

As illustrated in FIG. 18, the shaft 92 is made of rigid resin and extends in substantially a rod-like shape. One end of the shaft 92 is inserted into the cap 93, and the other end thereof is inserted into a conduit of the ultrasound endoscope 2. The shaft 92 moves in the conduit to switch between air/water supply conduits of the ultrasound endoscope 2.

The cap 93 includes a first member 931 having a hollow circular disk shape and a second member 932 provided inside the first member 931. The first member 931 and the second member 932 are made of rigid resin. A pressing surface 93*a*, which is pressed by the operator, is formed on one surface (the upper surface in FIGS. 17A and 17B) in a state where the first member 931 and the second member 932 are engaged with each other. A shaft hole 932*a* is formed on the surface of the second member 932 on the side opposite to the pressing surface 93*a*. The second member 932 includes a tubular rib 932*b* disposed on the outer periphery of the shaft hole 932*a*. The cap 93 is joined to the shaft 92 by ultrasound welding.

Figure 19A:
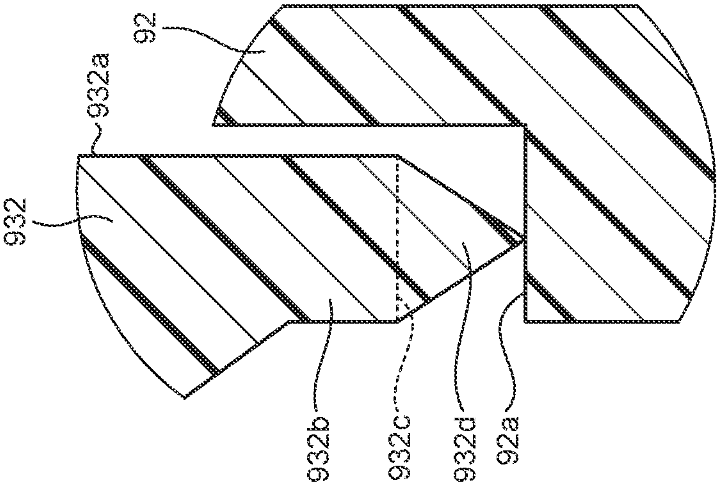
FIGS. 19A and 19B are a partially enlarged view of a region A3 in FIG. 18.
Figure 19B:
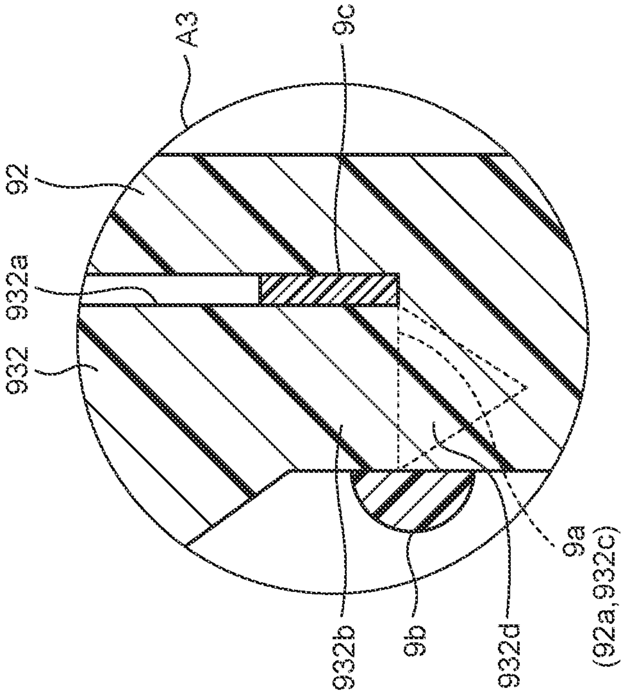

Next, a joint portion between the shaft 92 and the cap 93 is described. FIGS. 19A and 19B are a partially enlarged view of a region A3 in FIG. 18; FIG. 19A illustrates the region A3 before welding, and FIG. 19B illustrates the region A3 after welding. As illustrated in FIGS. 19A and 19B, a first welded portion (welded surface) 9*a* is disposed on an abutting surface 92*a* with the rib 932*b* of the shaft 92, and in this portion, a melted portion end 932*c* of the second member 932, which is melted by ultrasound vibration of the second member 932, is joined with an extreme surface portion of the shaft 92. Melted resin 932*d* of the second member 932, which is melted by ultrasound vibration, flows out separately as resin 9*b* and resin 9*c* to the outer peripheral side and the inner peripheral side of the first welded portion (the welded surface) 9*a* so as to cover and reinforce the joint portion between the second member 932 and the shaft 92 like an adhesive. Particularly, as the resin 9*c* acts as a force in the shearing direction against the force in the pulling direction of the second member 932 with respect to the shaft 92, the adhesive strength is increased.

Figure 20B:
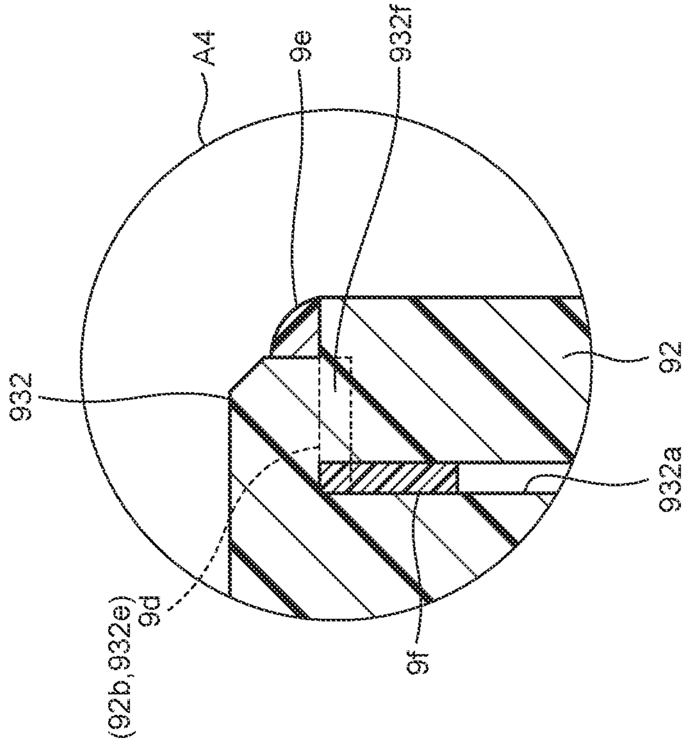
FIGS. 20A and 20B are a partially enlarged view of a region A4 in FIG. 18.
Figure 20A:
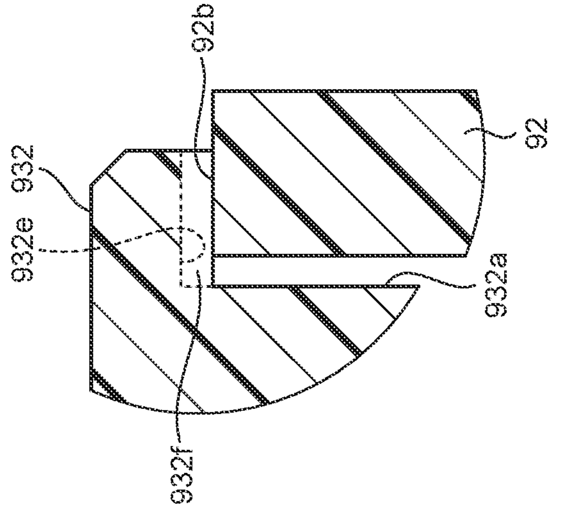

FIGS. 20A and 20B are a partially enlarged view of a region A4 in FIG. 18; FIG. 20A illustrates the region A4 before welding, and FIG. 20B illustrates the region A4 after welding. As illustrated in FIGS. 20A and 20B, a second welded portion (welded surface) 9*d* is disposed on a distal end 92*b* of the shaft 92, and in this portion, a melted portion end 932*e* of the second member 932, which is melted by ultrasound vibration of the second member 932, is joined with an extreme surface portion of the shaft 92. Melted resin 932*f* of the second member 932, which is melted by ultrasound vibration, flows out separately as resin 9*e* and resin 9*f* to the outer peripheral side and the inner peripheral side of the second welded portion (the welded surface) 9*d* so as to cover and reinforce the joint portion between the second member 932 and the shaft 92 like an adhesive. Particularly, as the resin 9*f* acts as a force in the shearing direction against the force in the pulling direction of the second member 932 with respect to the shaft 92, the adhesive strength is increased.

As described in FIGS. 18 to 20, the first welded portion 9*a* and the second welded portion 9*d* are spaced apart from each other along the direction in which the shaft 92 extends. It is preferable that the first welded portion 9*a* and the second welded portion 9*d* are spaced apart from each other by more than half of the radius of the circular pressing surface 93*a* of the cap 93 along the direction in which the shaft 92 extends. As a result, even when the position near the outer periphery of the circular pressing surface 93*a* is pressed and a force is applied in such a direction to incline the cap 93 with respect to the central axis Ax2, the cap 93 and the shaft 92 are prevented from being separated from each other as the cap 93 and the shaft 92 are joined to each other at two positions (the first welded portion 9*a* and the second welded portion 9*d*) along the direction in which the shaft 92 extends.

The disposable conduit switching device (the suction button 10) for an endoscope according to the embodiment described above adopts the structure to switch between the connection states of the conduits 6 by a two-step pressing operation; however, this is not a limitation, and the disposable conduit switching device for an endoscope may adopt the structure to enable only a one-step pressing operation.

In the description according to the above-described embodiment, the endoscope system 1 has both the function to generate an ultrasound image and the function to generate an endoscopic image; however, this is not a limitation, and the endoscope system 1 may be configured to have only the function to generate an ultrasound image.

In the embodiment described above, the endoscope system 1 may be an endoscope system that observes the inside of the subject such as a mechanical structure in the industrial field as well as in the medical field.

According to the disclosure, it is possible to produce a disposable conduit switching device for an endoscope in which a cap and a shaft made of resin are prevented from being separated from each other.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope conduit switching device comprising:

a cap made of resin, the cap including a pressing surface pressed by an operator and a shaft hole formed on a surface of the cap on a side opposite to the pressing surface; and a shaft having one end inserted into the shaft hole of the cap and an other end inserted into a conduit of the endoscope, wherein the cap is joined to the one end of the shaft at first and second joint portions, the first joint portion and the second joint portion are spaced apart from each other along a direction in which the shaft extends; and portions of the shaft and shaft hole between the first and second joint portions are not joined, wherein the shaft is made of resin;

the shaft and the shaft hole defining an annular gap;

the first joint portion is disposed in a first portion of the annular gap;

the second joint portion is disposed in a second portion of the annular gap; and a third portion of the annular gap between the first portion and the second portion is not filled by either the first joint portion or the second joint portion.

2. The endoscope conduit switching device according to claim 1, wherein the cap includes a tubular rib that is disposed on an outer periphery of the shaft hole.

3. The endoscope conduit switching device according to claim 2, wherein the first joint portion is disposed at an end face of the rib, and the second joint portion is disposed at a distal end of the shaft on a side of the cap.

4. The endoscope conduit switching device according to claim 1, wherein the first joint portion and the second joint portion are spaced apart from each other by more than half of a radius of the pressing surface of the cap along the direction in which the shaft extends.

5. The endoscope conduit switching device according to claim 1, wherein the shaft is configured to move in the conduit to switch between suction conduits of the endoscope.

6. The endoscope conduit switching device according to claim 1, further comprising:

an attachment to be attached to the endoscope;

a movable spring bearing that is movably held by the attachment, the movable spring bearing being configured to movably hold the shaft;

a movable piston that is secured to the movable spring bearing and is movable to be inserted or removed with respect to a different conduit of the endoscope;

a first coil spring having an end abutting the movable spring bearing and an other end abutting the cap, the first coil spring being configured to bias the movable spring bearing and the cap in directions away from each other; and a second coil spring having an end abutting the attachment and an other end abutting the movable spring bearing, the second coil spring being configured to bias the attachment and the movable spring bearing in directions away from each other.

7. The endoscope conduit switching device according to claim 6, wherein in accordance with an operation on the cap, the shaft is configured to move relative to the movable spring bearing so as to make a first conduit of the endoscope communicate, and in accordance with an operation on the cap, the movable piston is configured to move together with the movable spring bearing relative to the attachment so as to make a second conduit of the endoscope communicate.

8. The endoscope conduit switching device according to claim 1, wherein the endoscope conduit switching device is detachably attached to the endoscope.

9. The endoscope conduit switching device according to claim 1, wherein the first joint portion and the second joint portion are a first welded portion and a second welded portion, respectively, which are joined by welding.

10. The endoscope conduit switching device according to claim 9, wherein at least one of the first and second joint portions being covered with resin.

11. The endoscope conduit switching device according to claim 10, wherein the resin covering the at least one of the first and second joint portions joins surfaces of the shaft hole and the shaft facing each other in a direction that intersects with the direction in which the shaft extends.

12. The endoscope conduit switching device according to claim 10, wherein the resin covering the at least one of the first and second joint portions joins surfaces of the shaft hole and the shaft along the direction in which the shaft extends.

13. The endoscope conduit switching device according to claim 1, wherein the endoscope conduit switching device is a disposable component.

* * * * *